(12) United States Patent
Wang et al.

(10) Patent No.: US 9,221,747 B2
(45) Date of Patent: Dec. 29, 2015

(54) METHOD OF MAKING FATTY ACID N-ACYLALKANOLAMINES

(71) Applicant: Iowa State University Research Foundation, Inc., Ames, IA (US)

(72) Inventors: Tong Wang, Ames, IA (US); Xiaosan Wang, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 228 days.

(21) Appl. No.: 13/869,099

(22) Filed: Apr. 24, 2013

(65) Prior Publication Data

US 2013/0303795 A1    Nov. 14, 2013

Related U.S. Application Data

(60) Provisional application No. 61/638,250, filed on Apr. 25, 2012.

(51) Int. Cl.
 C07C 231/00   (2006.01)
 C12P 13/00    (2006.01)
 C07C 231/02   (2006.01)

(52) U.S. Cl.
 CPC ................................. *C07C 231/02* (2013.01)

(58) Field of Classification Search
 CPC .. C07C 231/02; C07C 231/12; C07C 231/08; A61Q 19/00; A61K 8/42; C12P 13/001; C12P 13/02; C12P 13/04; C12P 13/004; C12N 9/88
 USPC ................. 554/68, 69, 70; 435/128
 See application file for complete search history.

(56) References Cited

U.S. PATENT DOCUMENTS 6,911,474 B2   6/2005  Piomelli et al.
7,423,066 B2   9/2008  Piomelli et al.
(Continued)

OTHER PUBLICATIONS

Wang et al., "Synthesis of Oleoylethanolamdie Using Lipase", Journal of Agricultural and Food Chemistry, 60, 451-457, 2012.*
(Continued)

*Primary Examiner* — Deborah D Carr
(74) *Attorney, Agent, or Firm* — LeClairRyan

(57) ABSTRACT

The present invention relates to methods for making a fatty acid N-acylalkanolamine having the formula:

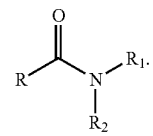

One of the methods comprises the steps of providing a vinyl ester of a fatty acid having the formula:

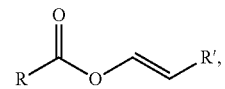

providing a primary or secondary alkanolamine having the formula: $NHR_1R_2$; and reacting the vinyl ester of the fatty acid with the alkanolamine under conditions effective to form the fatty acid N-acylalkanolamine. The other method comprises the steps of providing a fatty acid; purifying the fatty acid; providing a primary or secondary alkanolamine having the formula: $NHR_1R_2$; reacting the fatty acid with the alkanolamine under conditions effective to form the fatty acid N-acylalkanolamine; and purifying the formed fatty acid N-acylalkanolamine.

24 Claims, 14 Drawing Sheets

(56) References Cited

U.S. PATENT DOCUMENTS

| | | |
|---|---|---|
| 2005/0054730 A1 | 3/2005 | Fu et al. |
| 2005/0154064 A1 | 7/2005 | Piomelli et al. |
| 2005/0187254 A1 | 8/2005 | Piomelli et al. |
| 2009/0054526 A1 | 2/2009 | Hansen et al. |

OTHER PUBLICATIONS

Kawamura et al., "Sucrose Monoesters of Lauric, Palmitic or Stearic Acid," Compendium of Food Additive Specifications, The Joint FAO/WHO Expert Committee on Food Additives, 73rd Meeting 2010 (Jun. 8-17, 2010).

Kawamura et al., "Sucrose Monoesters of Lauric, Palmitic or Stearic Acid," Compendium of Food Additive Specifications, The Joint FAO/WHO Expert Committee on Food Additives, 74th Meeting 2011 (Jun. 14-23, 2011).

Wang et al., "An Improved Method for Synthesis of N-stearoyl and N-palmitoylethanolamine," J. Am. Oil Chem. Soc. 89(7):1305-1313 (2012).

Wang et al., "Synthesis of Oleoylethanolamide Using Lipase," J. Agric. Food Chem. 60:451-457 (2012).

Wang et al., "Improved Synthesis Methods for N-Acylethanolamines," Abstract, ISU Technology Transfer Online Publication (Jul. 26, 2012).

Wang et al., "Enrichment of Arachidonic Acid for the Enzymatic Synthesis of Arachidonoyl Ethanolamide," J. Am. Oil Chem. Soc. 90:1031-1039 (2013).

* cited by examiner

Main reaction:
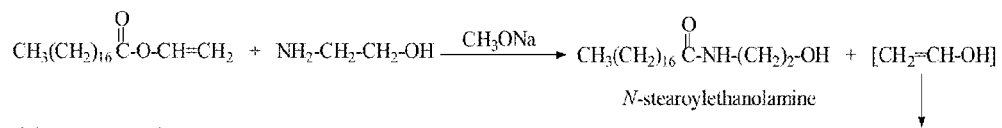
N-stearoylethanolamine
Side reactions:
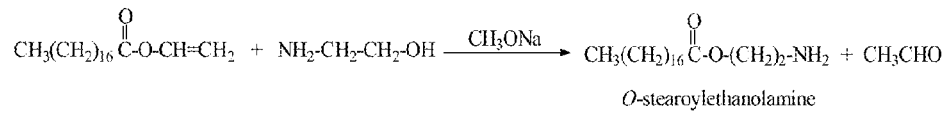
O-stearoylethanolamine
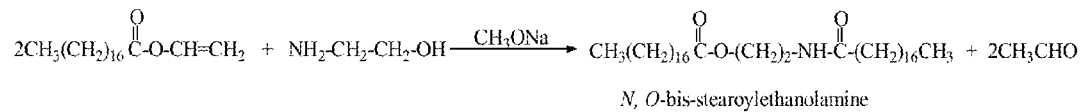
N, O-bis-stearoylethanolamine
*FIG. 6*

MAIN REACTION:

$$CH_3(CH_2)_7CH=CH(CH_2)_7-\overset{O}{\overset{\|}{C}}-O-H + NH_2-CH_2-CH_2-OH \underset{}{\overset{NOVOZYM\ 435}{\rightleftharpoons}} CH_3(CH_2)_7CH=CH(CH_2)_7-\overset{O}{\overset{\|}{C}}-NH-CH_2-CH_2-OH + H_2O$$

OLEOYL ETHANOLAMIDE

SIDE REACTIONS:

$$CH_3(CH_2)_7CH=CH(CH_2)_7-\overset{O}{\overset{\|}{C}}-O-H + NH_2-CH_2-CH_2-OH \underset{}{\overset{NOVOZYM\ 435}{\rightleftharpoons}} CH_3(CH_2)_7CH=CH(CH_2)_7-\overset{O}{\overset{\|}{C}}-O-CH_2-CH_2-NH_2 + H_2O$$

OLEOYL ESTERAMINE $$2CH_3(CH_2)_7CH=CH(CH_2)_7-\overset{O}{\overset{\|}{C}}-O-H + NH_2-CH_2-CH_2-OH \underset{}{\overset{NOVOZYM\ 435}{\rightleftharpoons}} CH_3(CH_2)_7CH=CH(CH_2)_7-\overset{O}{\overset{\|}{C}}-O-CH_2-CH_2-NH-\overset{O}{\overset{\|}{C}}(CH_2)_7CH=CH(CH_2)_7CH_3 + H_2O$$

OLEOYL ESTERAMIDE

*FIG. 9*

METHOD OF MAKING FATTY ACID N-ACYLALKANOLAMINES

This application claims the benefit of U.S. Provisional Patent Application Ser. No. 61/638,250, filed Apr. 25, 2012, which is hereby incorporated by reference in its entirety.

FIELD OF THE INVENTION

The present invention relates to methods for making a fatty acid N-acylalkanolamine, with a high yield and high purity, from the reaction of an alkanolamine with the corresponding fatty acid or with an vinyl ester of the corresponding fatty acid.

BACKGROUND OF THE INVENTION

N-acylethanolamines from fatty acids are an important class of alkanolamides that function as nonionic surfactants and have a wide range of applications in the lubricants, surfactants and detergents, cosmetics, and other industries (Liu et al., *J. Agric. Food. Chem.* 49:5761-64 (2001); Sanders, *J. Am. Oil Chem. Soc.* 35:548-51 (1958); Feairheller et al., *J. Am. Oil Chem. Soc.* 71:863-66 (1994)). Certain N-acylethanolamines are lipid mediators in animals and plants (Kilaru et al., *Chem. Biodivers.* 4:1933-55 (2007); Re et al., *Vet. J.* 173:21-30 (2007); Terrazzino et al., *FASEB J.* 18:1580 (2004)). It has been reported that N-acylethanolamines of different chain length and structure exhibited a variety of biological activities. N-palmitoylethanolamine had anti-inflammatory activity, and attenuates pain sensation (Re et al., *Vet. J.* 173:21-30 (2007); Calignano et al., *Nature* 394:277-81 (1998)). It was also shown to reduce allergic reaction, inhibit mast cell degranulation (Aloe et al., *Inflamm. Res.* 39:145-47 (1993)) and exert neuroprotective effects in rats and mice (Lambert et al., *Epilepsia* 42:321-27 (2001)). These actions were accompanied by changes in nitric oxide production (Ross et al., *Eur. J. Pharmacol.* 401:121-30 (2000)) and the expression of pro-inflammatory proteins (Costa et al., *Br. J. Pharmacol.* 137:413-20 (2002)). N-stearoylethanolamine showed pro-apoptotic and anorexic effects (Okamoto et al., *Chem. Biodivers.* 4:1842-57 (2007)). It could affect cell signaling and elicit biological effects potentially through targets other than cannabinoid receptors, such as exerting anorexic effects in mice via down-regulation of a liver enzyme expression (Terrazzino et al., *FASEB J.* 18:1580 (2004)), and having anti-inflammatory activity by a passive IgE-induced cutaneous anaphylaxis (Ezzili et al., *Bioorg. Med. Chem. Lett.* 20:5959-68 (2010)). N-oleoylethanolamine exerted anorexigenic effects by binding to the nuclear receptor in the periphery tissues, leading to body fat loss (Thabuis et al., *Lipids* 43:887-94 (2008); Astarita et al., *J. Pharmacol. Exp. Ther.* 318:563 (2006)).

N-acylethanolamines from fatty acids were typically synthesized by reacting fatty acid chloride (Giuffrida et al., *Eur. J. Pharmacol.* 408:161-68 (2000); Koutek et al., *J. Biol. Chem.* 269:22937-40 (1994)), fatty acid methyl ester (Farris, *J. Am. Oil Chem. Soc.* 56:770-73 (1979); Maag, *J. Am. Oil Chem. Soc.* 61:259-67 (1984)) or triacylglycerol (Lee et al., *J. Am. Oil Chem. Soc.* 84:945-52 (2007)) with an alkanolamine, or by a direct reaction between free fatty acid and an alkanolamine in the presence of a catalysts at a low temperature or without any catalyst at a high temperature (Liu et al., *J. Agric. Food. Chem.* 49:5761-64 (2001)). Yield and purity improvement was usually achieved by removal of water, methanol, glycerol or hydrochloric acid. However, only 60-90% N-acylethanolamines were produced from free fatty acid, fatty acid methyl ester and triacylglycerol at the temperature above 100° C., usually at 180° C. for 6-12 hours (Tufvesson et al., *Biotechnol. Bioeng.* 97:447-53 (2007)). It has been reported that about 99% N-acylethanolamine was obtained if two moles of fatty acid and one mole of ethanolamine were first reacted at 180° C. to give the N,O-bis-acylethanolamine, which was then transesterified with another mole of ethanolamine to form the N-acylethanolamine (Maag, *J. Am. Oil Chem. Soc.* 61:259-67 (1984)). Nevertheless, this reaction was conducted at a high temperature, which resulted in the formation of products with dark color that significantly influences the product's quality. The addition of deodorizers and antioxidants has been suggested to improve the quality of final products (Tufvesson et al., *Biotechnol. Bioeng.* 97:447-53 (2007)). The main problems for synthesis of N-acylethanolamines are the low conversion of the reactants and the esterification reaction occurred during the reaction, which result in a low yield of N-acylethanolamines.

Purity of commercial alkanolamides for surfactant purposes was about 80% (Khanmohammadi et al., *J. Surfactants Deterg.* 12:37-41 (2009)), but with the increasing knowledge and interest in N-acylethanolamines as lipid mediators in animals, plants, or humans, high purity N-acylethanolamines are needed to validate their biological functions in cellular and animal systems. Currently, this type of study is limited to small animal experiments due to the lack of access to these compounds in a desired purity and quantity. For example, the price of N-stearoyl and N-palmitoylethanolamines from the Sigma Chemical Company is $82/5 mg and $60.8/10 mg. Thus, it is necessary to establish a simple, efficient, effective and economical synthesis method to support the investigation of biological and nutritional properties of N-acylethanolamines in large animals and human subjects.

The present invention is directed to fulfilling these needs in the art.

SUMMARY OF THE INVENTION

One aspect of the present invention relates to a method for making a fatty acid N-acylethanolamine having the formula:

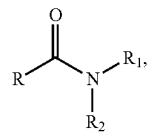

where

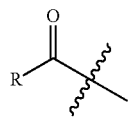

is derived from a natural or synthetic fatty acid; $R_1$ is a substituted or unsubstituted $C_1$ to $C_{10}$ hydroxyalkyl; and $R_2$ is H, $R_1$ or a $C_1$ to $C_{10}$ hydrocarbon radical. The method comprises the step of providing a vinyl ester of a fatty acid having the formula:

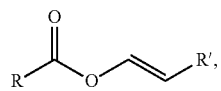

where R' is H, a branched or unbranched, substituted or unsubstituted $C_1$ to $C_6$ alkyl or $C_2$ to $C_6$ alkenyl. A primary or secondary alkanolamine having the formula: $NHR_1R_2$ is also provided. The vinyl ester of the fatty acid is reacted with the alkanolamine under conditions effective to form the fatty acid N-acylalkanolamine.

Another aspect of the present invention relates to a method for making a fatty acid N-acylalkanolamine having the formula:

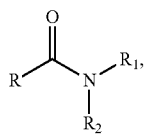

where

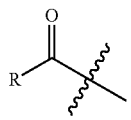

is derived from a natural or synthetic fatty acid; $R_1$ is a substituted or unsubstituted $C_1$ to $C_{10}$ hydroxyalkyl; and $R_2$ is H, $R_1$, or a $C_1$ to $C_6$ hydrocarbon radical. The method comprises the steps of providing a fatty acid and purifying the fatty acid. A primary or secondary alkanolamine having the formula: $NHR_1R_2$ is also provided. The purified fatty acid is reacted with the alkanolamine under the conditions effective to form the fatty acid N-acylalkanolamine. The formed fatty acid N-acylalkanolamine is further purified.

In the present invention, a novel method for the preparation of high-purity fatty acid N-acylalkanolamine, such as N-stearoyl and N-palmitoylethanolamines, is presented. A vinyl ester of a fatty acid is used as an acyl donor to investigate the reaction conditions and the effects of the catalyst type and concentrations, substrate ratio, solvent, temperature, and reaction time on the purity of N-acylalkanolamine. For example, a reaction carried out by using an excess amount of ethanolamine, which acted as both reactant and solvent, in the presence of sodium methoxide catalyst at a mild temperature resulted in the formation of high purity N-stearoyl and N-palmitoylethanolamine. The use of fatty acid vinyl ester led to an irreversible reaction, because the volatile acetaldehyde by-product was easily removed. Complete conversion of vinyl stearate and palmitate was achieved.

Additionally, a process for enzymatic synthesis of fatty acid N-acylalkanolamine, such as an oleoyl ethanolamide, is described. An example of this process includes purification of a raw oleic acid and an amidation reaction between the purified oleic acid and ethanolamine in hexane in the presence of a lipase. Compared to the previous studies, this method produces an oleoyl ethanolamide of very high purity, and is more effective and economically feasible. This method is more economical, because of the low cost of oleic acid and more efficient, because the lipase has a high selectivity for the amidation reaction. The method is suitable for a large-scale synthesis in a quantity needed for research and development of biological and nutritional functions in animal or human systems.

BRIEF DESCRIPTION OF THE DRAWINGS

FIG. 6 is a scheme showing possible reactions between ethanolamine and vinyl stearate.

FIG. 9 is a scheme showing possible reactions between ethanolamine and oleic acid.

DETAILED DESCRIPTION OF THE INVENTION

Definitions

Figure 1:
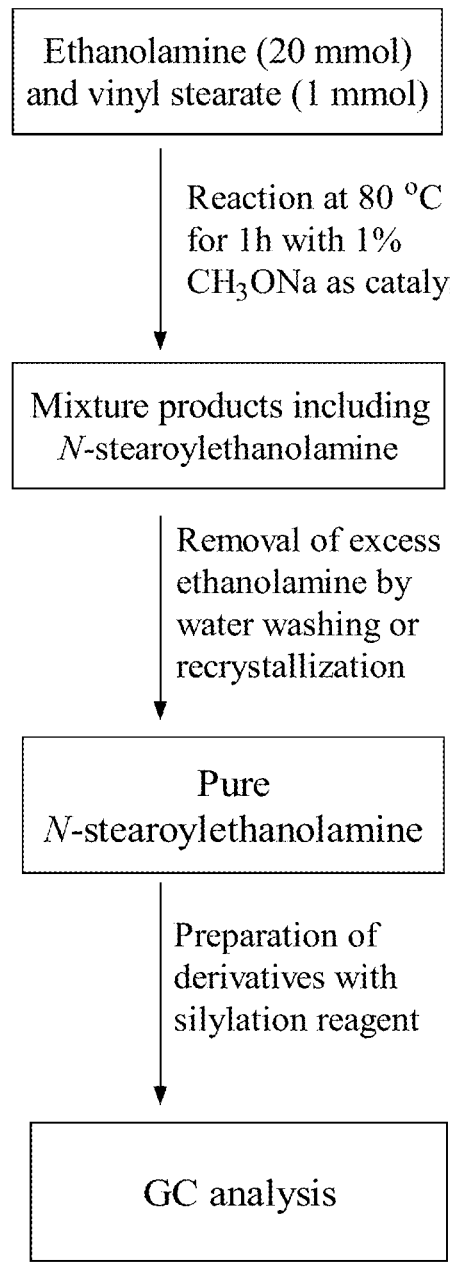
FIG. 1 is a flow chart showing the general synthetic procedures for N-stearoylethanolamine.

As used herein, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

"Hydrocarbon radical" typically consists only of carbon and hydrogen. The term used herein typically includes aliphatic hydrocarbon radicals (e.g., alkane, alkene or alkyne) may be linear (unbranched), branched or cyclic hydrocarbon structure, and saturated or unsaturated. Branched hydrocarbon means that one or more lower alkyl groups such as methyl, ethyl, or propyl are attached to a linear hydrocarbon chain.

The term "alkyl" refers to an aliphatic hydrocarbon group which may be a linear (unbranched), branched, or cyclic hydrocarbon structure or combination thereof. Representative alkyl groups are those having 24 or fewer carbon atoms, for instance, methyl, ethyl, n-propyl, i-propyl, n-butyl, s-butyl, t-butyl, n-pentyl, i-pentyl, n-hexyl, and the like. Lower alkyl refers to alkyl groups having about 1 to about 6 carbon atoms, or having about 1 to about 4 carbon atoms, in the chain. Branched alkyl means that one or more lower alkyl groups such as methyl, ethyl, or propyl are attached to a linear alkyl chain.

The statement that alkyl is intended to include linear, branched, or cyclic hydrocarbon structures and combinations thereof means that an "alkyl" group also includes the combinations of linear and cyclic structural elements.

The term "alkenyl" means an aliphatic hydrocarbon group containing at least one double bond between adjacent carbon atoms. Alkenyls include both cis and trans isomers. Branched alkenyl means that one or more lower alkyl groups such as methyl, ethyl, or propyl are attached to a linear alkenyl chain. Representative straight chain and branched alkenyls are those having about 2 to about 6 carbon atoms, or about 2 to about 4 carbon atoms, in the chain, for instance, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

The term "hydroxyalkyl" refers to a branched or straight-chain (unbranched) alkyl as described above, substituted with one or more hydroxy groups.

The term "acyl" refers to groups of from 1 to 8 carbon atoms of a straight, branched, or cyclic configuration, saturated, unsaturated, or aromatic, and combinations thereof, attached to the parent structure through a carbonyl functionality. One or more carbons in the acyl residue may be replaced by nitrogen, oxygen, or sulfur as long as the point of attachment to the parent remains at the carbonyl. Examples include acetyl (Ac), propionyl, isobutyryl, t-butoxycarbonyl, and the like.

The term "fatty acid" generally refers to a carboxylic acid which bears a hydrocarbon radical. Typically, the term is used in the sense of monocarboxylic acid. The hydrocarbon radical has been described above, and can have from about 1 to 50 carbon atoms in length. Typical fatty acids have 2 to 50 carbon atoms, 4 to 50 carbon atoms, 4 to 30 carbon atoms, 4 to 26 carbon atoms, 8 to 26 carbon atoms, 8 to 24 carbon atoms, 8 to 22 carbon atoms, 12 to 22 carbon atoms, 12 to 18 carbon atoms and 14 to 22 carbon atoms. They may be of a natural or synthetic origin. Fatty acids can be saturated, unsaturated, or polyunsaturated. When they are unsaturated, they may contain one or more, for example two, three or more, double bonds.

The above terms "hydrocarbon radical", "alkyl", "alkenyl", "hydroxyalkyl", and "fatty acid" may be optionally substituted, substituted or unsubstituted.

The term "substituted" or "optionally substituted" is used to indicate that a group may have a substituent at each substitutable atom of the group (including more than one substituent on a single atom), provided that the designated atom's normal valency is not exceeded and the identity of each substituent is independent of the others. In accordance with the present invention, up to three H atoms in each residue can be replaced with alkyl, halogen, haloalkyl, alkyenyl, haloalkenyl, cycloalkyl, cycloalkenyl, hydroxy, alkoxy, acyl, carboxy, carboalkoxy (also referred to as alkoxycarbonyl), carboxamido (also referred to as alkylaminocarbonyl), cyano, carbonyl, nitro, amino, alkylamino, dialkylamino, acylamino, amidino, mercapto, alkylthio, sulfoxide, sulfone, and/or sulfonic acid groups. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious agent.

In the characterization of some of the substituents, certain substituents may combine to form rings. Unless stated otherwise, it is intended that such rings may exhibit various degrees of unsaturation (from fully saturated to fully unsaturated), may include heteroatoms, and may be substituted with other substituent groups as described above.

The compounds described herein may contain one or more asymmetric centers and may thus give rise to enantiomers, diastereomers, and other stereoisomeric forms. Each chiral center may be defined, in terms of absolute stereochemistry, as (R)— or (S)—. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration; thus a carbon-carbon double bond depicted arbitrarily herein as trans may be Z, E, or a mixture of the two in any proportion.

One aspect of the present invention relates to a method for making a fatty acid N-acylethanolamine having the formula:

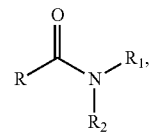

where

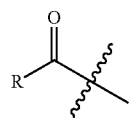

is derived from a natural or synthetic fatty acid; $R_1$ is a substituted or unsubstituted $C_1$ to $C_{10}$ hydroxyalkyl; and $R_2$ is H, $R_1$ or a $C_1$ to $C_{10}$ hydrocarbon radical. The method comprises the step of providing a vinyl ester of a fatty acid having the formula:

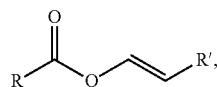

where R' is H, a branched or unbranched, substituted or unsubstituted $C_1$ to $C_6$ alkyl or $C_2$ to $C_6$ alkenyl. A primary or secondary alkanolamine having the formula: $NHR_1R_2$ is also provided. The vinyl ester of the fatty acid is reacted with the alkanolamine under conditions effective to form the fatty acid N-acylalkanolamine.

Vinyl esters of a fatty acid used in accordance with this method have the formula:

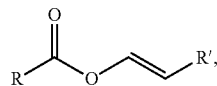

where

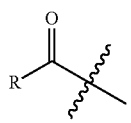

is derived from a natural or synthetic fatty acid; and R' is H, a branched or unbranched, substituted or unsubstituted $C_1$ to $C_6$ alkyl or $C_2$ to $C_6$ alkenyl. The amidation reaction of the fatty acid vinyl ester with the primary or secondary alkanolamine dominates and results in the formation of N-acylethanolamines and

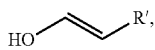

which consequently tautomerizes to a non-nucleophilic

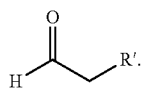

Easy removal of the resulting aldehyde

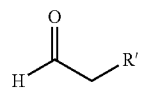

from the reaction system accelerates the reaction and promotes the reaction to complete. It is desirable that the resulting

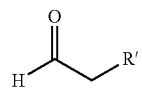

can be evaporated under the reaction temperature. In one embodiment, R' is a branched or unbranched, substituted or unsubstituted $C_1$ to $C_4$ alkyl or $C_2$ to $C_4$ alkenyl. In another embodiment, R' is H.

The fatty acid vinyl esters used herein may be commercially available, or prepared by methods known to one skilled in the art. For instance, the corresponding fatty acids can be esterified with the corresponding vinyl ester in the presence of a catalyst. For instance, when R' is H, the fatty acid vinyl ester may be prepared by reacting vinyl acetate and the corresponding fatty acids in the presence of a catalyst. See, also U.S. Pat. Nos. 2,066,075 and 2,989,554, which are hereby incorporated by reference in their entirety.

The parent fatty acid

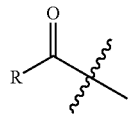

may be derived from a natural or synthetic fatty acid. The term "fatty acid" has been described herein. Typical fatty acid used herein contains between 4 to 50 carbon atoms, for instance, 4 to 26 carbon atoms, 8 to 26 carbon atoms, 8 to 22 carbon atoms, 14 to 22 carbon atoms, or 12 to 18 carbon atoms. The fatty acid for the fatty acid vinyl ester used herein can vary depending on the desired fatty acid N-acylalkanolamine. Exemplary fatty acids include butyric acid, caproic acid, caprylic acid, capric acid, decenoic acid, lauric acid, cis-9-dodecenoic acid, myristic acid, myristoleic acid, cis-9-tetradecenoic acid, pentadecanoic acid, palmitic acid, palmitoleic acid, cis-9-hexadecenoic acid, heptadecanoic acid, heptadecenoic acid, stearic acid, oleic acid, linoleic acid, linolenic acid, ricinoleic acid, dihydroxystearic acid, nonadecanoic acid, arachidic acid, cis-9 acid, cis-11-eicosenoic acid, eicosadienoic acid, eicosatrienoic acid, arachidonic acid, eicosapentaenoic acid, behenic acid, erucic acid, docosadienoic acid, 4,8,12,15,19-docosapentaenoic acid, docosahexaenoic acid, lignoceric acid, tetracosenoic acid and mixtures thereof. Additionally, suitable fatty acids are fatty acid mixtures obtained from natural fats and oils, for example cottonseed oil, coconut oil, peanut oil, safflower oil, corn oil, palm kernel oil, rapeseed oil, castor oil, olive oil, mustardseed oil, soybean oil, sunflower oil, and tallow oil, bone oil, fish oil, or tall oil.

This method can generally be used for preparing N-acylalkanolamides of fatty acids that are saturated, unsaturated, or polyunsaturated. The method is especially suitable to prepare N-acylalkanolamides of the saturated fatty acids. Exemplary saturated fatty acids include, but are not limited to, palmitic acid, stearic acid, caprylic acid, capric acid, lauric acid, myristic acid, arachidic acid, behenic acid, lignoceric acid or cerotic acid. In one embodiment, the fatty acid is palmitic acid. In another embodiment, the fatty acid is stearic acid.

The alkanolamine used in the method of the present invention has the formula: $NHR_1R_2$. $R_1$ is a substituted or unsubstituted $C_1$ to $C_{10}$ hydroxyalkyl; and $R_2$ is H, $R_1$ or a $C_1$ to $C_{10}$ hydrocarbon radical. In one embodiment, $R_2$ is H. In another embodiment, $R_2$ is a substituted or unsubstituted $C_1$ to $C_{10}$ alkyl. In an additional embodiment, $R_2$ is a substituted or unsubstituted $C_1$ to $C_{10}$ hydroxyalkyl. Exemplary alkanolamines used in the method include, but are not limited to, ethanolamine, propanolamine, isopropanolamine, butanolamine, isobutanolamine, methylethanolamine, butylethanolamine, and mixtures thereof. A typical alkanolamine used in the reaction is ethanolamine, and the resulting fatty acid N-acylalkanolamine from the reaction is a fatty acid N-acylethanolamine.

According to the present invention, the reaction of vinyl ester of the fatty acid with the alkanolamine is typically carried out in a solvent-free system. Alkanolamine is typically used in an excess amount as both reactant and a solvent to dissolve the product fatty acid N-acylalkanolamine. Thus, the alkanolamine to the vinyl ester of the fatty acid molar ratio is higher than 1. The alkanolamine to the vinyl ester of the fatty acid molar ratio typically ranges from 5 to 25, for instance, from 10 to 25, from 15 to 25, or from 20 to 25.

At least one catalyst can be used in the reaction of the alkanolamine and the vinyl ester of the fatty acid. Generally, a basic catalyst, such as a metal alkoxide is used. Examples of suitable metal alkoxide include, but are not limited to, sodium methoxide, sodium ethoxide, sodium propoxide, potassium methoxide, potassium ethoxide, potassium propoxide, sodium butoxide, potassium butoxide, sodium pentoxide, potassium pentoxide, or mixtures thereof. The amount of metal alkoxide catalyst will be in a catalytically effective amount which can vary greatly. Depending on the other reaction parameters, a preferred amount of biocatalyst is one making complete conversion of the reactants within a period of from 1 to 96 hours, especially from 2 to 24 hours. Typically, metal alkoxide is present in a concentration ranging from 0.1 to 10 wt % of the total reactants, for instance, from 0.5 to 4 wt % of the total reactants, from 0.5 to 1 wt % of the total reactants, from 1 to 4 wt % of the total reactants, from 2 to 4 wt % of the total reactants, or from 3 to 4 wt % of the total reactants.

The reaction of the alkanolamine and the vinyl ester of the fatty acid can be carried out over a wide range of temperatures. Typically, this reaction is carried out at a temperature lower than 100° C., for instance, at a temperature ranging from 40 to 80° C., from 40 to 60° C., or from 60 to 80° C. Increasing the reaction temperature, for instance to be higher than 100° C. can result in an undesirable color and odor, which adversely affect the quality of the product fatty acid N-acylalkanolamine.

The duration of the reaction can be over a broad range of times. The advantage of reacting the alkanolamine and the vinyl ester of the fatty acid in accordance with the present invention includes the ability to obtain the desired fatty acid N-acylalkanolamine at a high yield and purity within a short reaction time. For instance, an almost complete conversion of stearic acid vinyl ester and palmitic acid vinyl ester to the corresponding fatty acid N-acylalkanolamines can be achieved in less than 1-1.5 hours. Prolonging the reaction time can make the reaction inefficient and may cause side reactions which reduce the yield and purity of the product fatty acid N-acylalkanolamine. Accordingly, the reaction is typically carried out in less than 4 hours, less than 3 hours, less than 2 hours, less than 1.5 hours, less than 1 hour, from 0.5 hour to 2 hours, or from 1 hour to 1.5 hours.

The method of preparing the fatty acid N-acylalkanolamine can optionally include a purification step. The purification step can be carried out by variety of methods including distillation, extraction, recrystallization, filtration, precipitation, or chromatography. Purification of the fatty acid N-acylalkanolamine prepared by the method of the present invention can be simply conducted by washing with water, recrystallization with appropriate solvent, or combinations thereof. For instance, removing the excess alkanolamine from the reaction system by simple water washing can improve the purity of the product fatty acid N-acylalkanolamine to higher than 95%.

The method according to the present invention allows very rapid and cost-effective preparation of fatty acid N-alkanolamides in very high yields and with very high purity.

In an exemplary embodiment, 20 mmol ethanolamine was reacted with 1 mmol vinyl stearate at 80° C. for 1 hour in the presence of 1% sodium methoxide. N-stearoylethanolamine with 96% purity was obtained after the removal of excess ethanolamine without further purification. In another exemplary embodiment, 20 mmol ethanolamine was reacted with 1 mmol vinyl palmitate at 60° C. for 1.5 hours in the presence of 1% sodium methoxide. N-palmitoylethanolamine with 98% purity was obtained after the removal of excess ethanolamine without further purification. More examples of reacting the alkanolamine and the vinyl ester of the fatty acid to prepare the high-purity fatty acid N-acylalkanolamine in a high yield are described in Examples 1-8.

Another aspect of the present invention relates to a method for making a fatty acid N-acylalkanolamine having the formula:

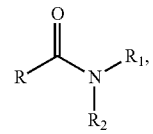

where

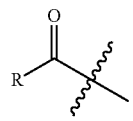

is derived from a natural or synthetic fatty acid; $R_1$ is a substituted or unsubstituted $C_1$ to $C_{10}$ hydroxyalkyl; and $R_2$ is H, $R_1$, or a $C_1$ to $C_6$ hydrocarbon radical. The method comprises the steps of providing a fatty acid and purifying the fatty acid. A primary or secondary alkanolamine having the formula: $NHR_1R_2$ is also provided. The purified fatty acid is reacted with the alkanolamine under the conditions effective to form the fatty acid N-acylalkanolamine. The formed fatty acid N-acylalkanolamine is further purified.

The fatty acid described above in the first aspect of the present invention can be used to carry out this aspect of the present invention.

This method can generally be used for preparing N-acylalkanolamides of fatty acids that are saturated, unsaturated, or polyunsaturated. The method is especially suitable to prepare N-acylalkanolamides of the unsaturated fatty acids. Exemplary unsaturated fatty acids include, but are not limited to, oleic acid, myristoleic acid, palmitoleic acid, sapienic acid, elaidic acid, vaccenic acid, linoleic acid, linoelaidic acid, α-linolenic acid, arachidonic acid, eicosapentaenoic acid, erucic acid, docosahexaenoic acid, or mixtures thereof. In one embodiment, the fatty acid is oleic acid.

The fatty acid is purified prior to reacting with the alkanolamine. A variety of methods can be used to obtain pure fatty acids, including chromatography, such as supercritical fluid chromatography (Pettinello et al., *J. Supercrit. Fluids*. 19:51-60 (2000), which is hereby incorporated by reference in its entirety); crystallization, such as low temperature crystallization (Patil & Nag, *J. Am. Oil. Chem. Soc.* 1-5 (2011), which is hereby incorporated by reference in its entirety); urea inclusion (Wu et al., *J. Am. Oil. Chem. Soc.* 85:677-84 (2008), which is hereby incorporated by reference in its entirety); and distillation, such as molecular distillation (Liang & Hwang, *J. Am. Oil. Chem. Soc.* 77:773-77 (2000), which is hereby incorporated by reference in its entirety). In one embodiment, the fatty acid is from a commercial source, and purified by low temperature crystallization to separate the desired fatty acid from other fatty acids.

The alkanolamine described above in the first aspect of the present invention can be used to carry out this aspect of the present invention.

According to the present invention, the reaction of the fatty acid with the alkanolamine is typically carried out in at least one solvent. In principle, it is possible to use any organic solvent which is inert under the reaction conditions employed and does not react with the reactants or the products formed. The solvents are typically non-polar organic solvents. The solvents can also be polar organic solvents; however, the solvents should not be too polar so that they do not react with the reactants or the products. Suitable solvents include, but are not limited to, organic ketones, such as acetone, methylethyl keone, or methyl isobutyl ketone; esters, such as methyl acetate, ethyl acetate, propyl acetate, or butyl acetate; ethers, such as ethyl ether, propyl ether, tetrahydrofuran (THF), or dioxane; hydrocarbon solvents, such as hexane, cyclohexane, benzene, toluene, xylene, ethylbenzene, tetralin, decane, pentadecane, or decalin; alkyl halides, such as ethylene dichloride, chloroform, or carbon tetrachloride; tertiary amines, such as dimethylformamide (DMF), pyridine, picoline, or methylpyrrolidone (NMP); and mixtures thereof. In one embodiment, the solvent is hexane.

When one or more solvents are present, the proportion thereof in the reaction mixture is preferably between 2% and 95% by weight, between 5% and 90% by weight, between 10% and 85% by weight, between 30% and 85% by weight, between 45% and 85% by weight, between 60% and 85% by weight, between 30% and 75% by weight, between 30% and 60% by weight, between 50% and 75% by weight, or between 60% and 75% by weight.

At least one catalyst can be used in the reaction of the alkanolamine and the fatty acid. In principle, any catalyst that can catalyze the reaction of an acid and amine to form an amide can be used herein. It is beneficial to use biocatalysts, because they are environmental friendly and incur less side reactions. A typical biocatalyst used herein is a lipase. Exemplary lipases used include, but are not limited to, Lipozyme TL IM, Novozym 435, Lipozyme IM 20, Lipase SP382, Lipase SP525, Lipase SP523, (all commercial products of Novozymes A/S, Bagsvaerd, Denmark), Chirazyme L2, Chirazyme L5, Chirazyme L8, Chirazyme L9 (all commercial products of Roche Molecular Biochemicals, Mannheim, Germany), and Lipase M "Amano", Lipase F-AP 15 "Amano", Lipase AY "Amano", Lipase N "Amano", Lipase R "Amano", Lipase A "Amano", Lipase D "Amano", Lipase G "Amano" (all commercial products of Amano, Japan).

The amount of the biocatalyst will be in a catalytically effective amount which can vary greatly. Depending on the other reaction parameters, a preferred amount of biocatalyst is one making complete conversion of the reactants within a period of from 1 to 96 hours, especially from 2 to 24 hours. Typically, lipase is present in a concentration ranging from 0.1 to 100 wt % of the total reactants, for instance, from 1 to 60 wt % of the total reactants, from 10 to 60 wt % of the total reactants, from 10 to 50 wt % of the total reactants, from 20 to 40 wt % of the total reactants, or from 20 to 30 wt % of the total reactants.

When enzymes are used as biocatalysts, generally they are employed in anhydrous or partially hydrated form for the catalytic activity (Irimescu et al., *J. Am. Oil. Chem. Soc.* 78:65-70 (2001), which is hereby incorporated by reference in its entirety). The lipase herein is used with a typical moisture content of 0 to 5%, 0 to 4%, 0.05% to 3%, 0.1% to 2%, 0.5% to 2%, 0.1% to 1%, or 0.5% to 1%.

The reaction of the alkanolamine and the fatty acid can be carried out over a wide range of temperatures. Typically, this reaction is carried out at a temperature lower than 100° C., particularly, at a temperature lower than 90° C., for instance, at a temperature ranging from 45 to 75° C., from 55 to 75° C., or from 65 to 75° C. Increasing the reaction temperature, for instance to be higher than 100° C., can result in an undesirable color and odor, which adversely affect the quality of the product fatty acid N-acylalkanolamine.

The duration of the reaction can be over a broad range of times. The advantage of reacting the alkanolamine and the fatty acid of the present invention includes the ability to obtain the desired fatty acid N-acylalkanolamine with a high yield and purity within a short reaction time. For instance, an almost complete conversion of oleic acid to the corresponding fatty acid N-alkanolamines can be achieved in less than 2 hours. Prolonging the reaction time can make the reaction inefficient, and may bring the side reactions, thus reducing the yield and purity of the product fatty acid N-acylalkanolamine. Accordingly, the reaction is typically carried out in less than 5 hours, less than 4 hours, less than 3 hours, less than 2 hours, for instance, from 1 hour to 5 hours, from 2 hour to 5 hours, or from 2 hour to 3 hours.

The method of preparing of the fatty acid N-acylalkanolamine further comprises a purification step. The purification step can be carried out by variety of methods including distillation, extraction, recrystallization, filtration, precipitation, or chromatography. In one embodiment, purification of the fatty acid N-acylalkanolamine prepared according to the method is simply conducted by recrystallization with appropriate solvents. For instance, a simple recrystallization of the product can improve the purity of the product fatty acid N-acylalkanolamine to higher than 95%.

The method according to the present invention allows very rapid, cost-effective, and environmental friendly preparation of fatty acid N-alkanolamides in very high yields and with very high purity.

In an exemplary embodiment, 1 mmol oleic acid was reacted with 1 mmol ethanolamine in 1.5 mL hexane at 65° C. for 3 hours in the presence 30% lipase and 10 μL water. N-oleoyl ethanolamine with 96.6% purity was obtained and all oleic acid was consumed. In another exemplary embodiment, when the synthesis was conducted on a large scale (50 mmol of each of the reactants), the purity of N-oleoyl ethanolamine after crystallization purification was 96.1%. More examples of reacting the alkanolamine and the fatty acid to prepare the high-purity fatty acid N-acylalkanolamine in a high yield are described in Examples 9-18.

The present invention may be further illustrated by reference to the following examples.

EXAMPLES

The following examples are for illustrative purposes only and are not intended to limit, in any way, the scope of the present invention.

Example 1

Experimental Materials

Most chemicals including N-acylethanolamines standards were purchased from the Sigma Aldrich Chemical Company (St. Louis, Mo.). Vinyl stearate and palmitate were purchased from Tokyo Chemical Industry (Tokyo, Japan). Ethanolamine (>99%) was purchased from Fisher Scientific (Fair Lawn, N.J.). *Candida antarctica* lipase (Novozym 435) was provided by Novozymes America (Blair, Nebr.). This is an immobilized lipase and has the declared activity of 10,000 PLU (propyl laurate unit)/g.

Example 2

Synthesis of N-stearoylethanolamine Using Vinyl Stearate Based on Procedures Described for Other Acyl Donors Amidation of Ethanolamine with Vinyl Stearate at 105° C. in a Solvent-Free System:

The procedure of Farris, *J. Am. Oil Chem. Soc.* 56:770-73 (1979), which is incoporated by reference in its entirety, in which fatty acid methyl ester was used as an acyl donor, was followed. Ethanolamine (1.1 mmol) was placed in a 10-mL round bottom flask and then vinyl stearate (1 mmol) was added followed by 0.5% sodium methoxide (w/w, relative to total reactants). The mixture was agitated at 105° C. Samples were withdrawn after 1 hour and 12 hours of reaction.

Amidation of Ethanolamine with Vinyl Stearate at 45° C. in Hexane:

This experiment was carried out followed the procedures of using free fatty acid as an acyl donor (Plastina et al., *Lett. Org. Chem.* 6:444-47 (2009), which is hereby incorporated by reference in its entirety). Ethanolamine (1 mmol) in hexane (5 mL) was mixed with vinyl stearate (1 mmol) in a 10-mL round bottom flask in the presence of Novozym 435 lipase at 10%, 20%, 30%, 40%, and 65% (relative to total reactants) level. Reaction was conducted with agitation at 45° C. for 5 hours and 20 hours before hexane was removed under reduced pressure. The enzyme was filtered out so that it can be reused if needed. The experiment was also conducted under similar conditions except that sodium methoxide was used at 1%, 2%, and 3% level, and that the reaction was carried out at ambient temperature (25° C.) for 14 hours.

Amidation of Ethanolamine with Vinyl Stearate at 50° C. in a Solvent-Free System:

The procedures of Kolancilar, *J. Am. Oil Chem. Soc.* 81:597-98 (2004), which is hereby incorporated by reference in its entirety in which laurel oil was used as an acyl donor, was followed. Vinyl stearate (1 mmol), ethanolamine (10 mmol), and sodium methoxide (2%, relative to total reactants) were placed in a 10-mL round bottom flask and the mixture was agitated at 50° C. for 2 hours and 3 hours. The reaction mixture was then mixed with 5 mL distilled water at 6° C. for 1 hour. This process was repeated three times to remove the excess ethanolamine.

After all reaction conditions, as described above, were examined, a set of conditions was identified for the synthesis of N-stearoyl and N-palmitoylethanolamines.

Example 3

Determining Conditions for the Amidation Reaction at Mild Temperature in a Solvent-Free System The experimental setup is outlined in Tables 1 and 2 and FIG. 1.

TABLE 1

Experimental setup for amidation reaction between vinyl stearate and ethanolamine[a]

| Level | $X_1$ (%, relative to total substrates) | $X_2$ (molar ratio) | $X_3$ (° C.) | $X_4$ (hour) |
|---|---|---|---|---|
| 1 | 0.5 | 5:1 | 40 | 0.5 |
| 2 | 1.0 | 10:1 | 50 | 1.0 |
| 3 | 2.0 | 15:1 | 60 | 2.0 |
| 4 | 3.0 | 20:1 | 70 | 3.0 |
| 5 | 4.0 | 25:1 | 80 | 4.0 |

[a]$X_1$: sodium methoxide. Reactions conducted by reacting 20 mmol ethanolamine with 1 mmol vinyl stearate at 60° C. for 1 hour; $X_2$: molar ratio of ethanolamine to vinyl stearate. Reactions conducted at 60° C. for 1 hour with 1% sodium methoxide $X_3$: temperature. Reactions conducted by reacting 20 mmol ethanolamine with 1 mmol vinyl stearate for 1 hour with 1% sodium methoxide; $X_4$: time. Reactions conducted by reacting with 20 mmol ethanolamine with 1 mmol vinyl stearate at 80° C. with 1% sodium methoxide.

TABLE 2

Experimental setup for amidation reaction between vinyl palmitate and ethanolamine[a]

| Level | $X_1$ (% by substrate) | $X_2$ (molar ratio) | $X_3$ (° C.) | $X_4$ (hour) |
|---|---|---|---|---|
| 1 | 1.0 | 5:1 | 40 | 0.5 |
| 2 | 2.0 | 10:1 | 50 | 1.0 |
| 3 | 2.5 | 15:1 | 60 | 1.5 |
| 4 | 3.0 | 20:1 | 70 | 2.0 |
| 5 | 3.5 | 25:1 | 80 | 2.5 |
| 6 | 4.0 | | | 3.0 |

[a]$X_1$: sodium methoxide. Reactions conducted by reacting 20 mmol ethanolamine with 1 mmol vinyl palmitate at 60° C. for 1 h; $X_2$: molar ratio of ethanolamine to vinyl palmitate. Reactions conducted at 60° C. for 1 hour with 3% sodium methoxide; $X_3$: temperature. Reactions conducted by reacting 20 mmol ethanolamine with 1 mmol vinyl stearate for 1 hour with 3% sodium methoxide; $X_4$: time. Reactions conducted by reacting with 20 mmol ethanolamine with 1 mmol vinyl stearate at 60° C. with 1% sodium methoxide.

The yields of N-stearoyl and N-palmitoylethanolamines were studied as a function of varying one of four variables while keeping the other three variables constant: sodium methoxide concentration, molar ratio of ethanolamine to fatty acid vinyl ester, reaction temperature and time.

To determine the catalyst concentration, ethanolamine (20 mmol) and vinyl stearate or palmitate (1 mmol) were mixed at 60° C. for 1 hour with different concentrations of sodium methoxide (0.5-4% for the synthesis of N-stearoylethanolamine, 1-4% for N-palmitoylethanolamine).

To determine the reactant ratio, different quantities of ethanolamine (5-25 mmol) were reacted with 1 mmol fatty acid vinyl ester at 60° C. for 1 hour. Sodium methoxide at 1% was used to determine the molar ratio of ethanolamine to vinyl stearate, while 3% sodium methoxide was used to determine the molar ratio of ethanolamine to vinyl palmitate as these catalyst concentrations were confirmed to be better concentrations for the two reactions.

After 20:1 molar ratio was confirmed as the optimal ratio for the synthesis, ethanolamine (20 mmol) and vinyl stearate or palmitate (1 mmol) were mixed at different temperatures (40-80° C.) for 1 hour with 1% or 3% sodium methoxide to determine the reaction temperature.

Moreover, ethanolamine (20 mmol) and vinyl stearate (1 mmol) were mixed at 80° C. with 1% sodium methoxide to determine the reaction time, as 80° C. was chosen as a better reaction temperature. The same ratio of reactants was mixed at 60° C. with 3% sodium methoxide to determine the reaction time for the N-palmitoylethanolamine synthesis.

For all the products, the excess ethanolamine was removed from the product by addition of distilled water (5 mL) and crystallization of the amide at 6° C. for one hour. N-acylethanolamines were washed three more times with water. All the above experiments were conducted in duplicate.

Example 4

Procedures for Preparing N-stearoyl and N-palmitoylethanolamines Derivatives The anhydrous reaction mixture containing amide (about 5 mg) was placed in 2 mL glass vial and treated with pyridine (0.5 mL), hexamethyldisilazane (0.15 mL) and trimethylchlorosilane (0.05 mL). The mixture was shaken for 15-30 seconds and then allowed to stand for 1 hour or stored in a freezer (0° C.) overnight, during which time the upper layer became clear (Wood et al., *J. Am. Oil Chem. Soc.* 42:161-65 (1965), which is hereby incorporated by reference in its entirety). N-stearoyl and N-palmitoylethanolamines standards were used as external standards and the peaks were identified according to gas chromatography (GC) retention time. Purity of N-acylethanolamines was calculated based on their peak areas relative to the total peak area of a particular sample.

Samples were identified and quantified by an HP 5890 Series II capillary GC (Hewlett-Packard, PA) equipped with a flame ionization detector (FID) using a 30 m×0.25 mm×0.25 μm (length×I.D.×film thickness) fused silica bonded phase capillary column SP-1 (Supelco, Bellefonte, Pa.). The carrier gas (helium) flow rate was 32.3 mL/min, and the split ratio was 7. The oven temperature was programmed from 140° C. to 300° C. at a rate of 10° C./min, and then held at 300° C. for 5 minutes. Injector and detector temperatures were set at 300° C.

Example 5

Purity Determination of N-stearoyl and N-palmitoylethanolamine Products by Thin-Layer Chromatography (TLC)

A developing solvent of A (toluene:ethyl acetate:ether:acetic acid=80:10:10:0.2, v/v) and B (100% methanol) in 80:15 ratio (v/v) were used to separate the products on a 20×20 cm silica plate (250 micrometer thickness), with the standards applied in separate lanes to further validate the purity of the water-washed final lipid products.

Example 6

NMR Analysis $^1$H-NMR qualitative analysis of N-stearoyl and N-palmitoylethanolamine products was conducted by using a Varian MR-400 Spectrometer (Foster City, Calif.) with CDCl$_3$ as solvent and tetramethylsilane (TMS) as the internal standard (chemical shift of 0 ppm).

Example 7

Selecting Reaction Parameters

The reaction conditions which were used for the synthesis of N-acylethanolamines in previous studies that used other acyl donors were tested in Examples 1-6, and the purity of N-acylethanolamines in the reaction mixture was used as a parameter to determine the reaction conditions. Because N-stearoylethanolamine has a high melting point (about 95° C.), amidation reaction between vinyl stearate and ethanolamine in a solvent-free system needs to be conducted at great than 95° C. or at a lower temperature in the presence of solvent and catalyst, such as a lipase or sodium methoxide.

When the amidation reaction was carried out at 105° C. in the solvent-free system, 67.9% and 73.0% N-stearoylethanolamine was obtained at 1 hour and 12 hours, respectively. The reaction after 12 hours did not result in a dramatic increase in N-stearoylethanolamine content compared to that at 1 hour. The reaction at 105° C. resulted in the formation of products with dark color, which influenced product quality.

Thereafter, reaction in a solvent system at lower temperature was tested. Results for the synthesis of N-stearoylethanolamine in the solvent system are presented in Table 3.

TABLE 3

Synthesis of N-stearoylethanolamine in a solvent system with lipase as catalyst

| | Time of reaction (h) | | | | | | | | | |
|---|---|---|---|---|---|---|---|---|---|---|
| | 5 | | | | | 20 | | | | |
| Lipase (% relative to total substrate) | 10 | 20 | 30 | 40 | 65 | 10 | 20 | 30 | 40 | 65 |
| Vinyl stearate (%) | 85.4 | 0 | 0 | 0 | 0 | 73.6 | 0 | 0 | 0 | 0 |
| O-stearoylethanolamine (%) | 7.2 | 100 | 100 | 100 | 17.4 | 5.3 | 100 | 100 | 100 | 26.5 |
| N-stearoylethanolamine (%) | 0 | 0 | 0 | 0 | 72.3 | 10.9 | 0 | 0 | 0 | 61.6 |

Although the previous researchers used these reaction conditions to synthesize N-acylethanolamine, the desired product was not formed herein under low concentration of lipase, when vinyl stearate was used as acyl donor. Instead, a side reaction product, O-stearoylethanolamine was produced in high concentration. When the enzyme concentration was increased to 65%, 72.3% N-stearoylethanolamine produced after 5 hours. Further enzyme addition was not feasible with this experiment. When the enzyme was substituted with sodium methoxide, no N-stearoylethanolamine was produced after 14 hours, with the catalyst concentrations at 1, 2 and 3% (w/w) level (based on total reactants).

Reactions using an excess ethanolamine as solvent to dissolve N-stearoylethanolamine were carried out next. When an excess ethanolamine (10×) was used to act as both reactant and the solvent to dissolve the N-stearoylethanolamine product, 92.9% N-stearoylethanolamine was produced with 2% sodium methoxide at 50° C. after 2 hours. This experiment proved that the N-stearoylethanolamine can be synthesized by using an excess ethanolamine as a solvent rather than using hexane probably, because hexane diluted the catalyst and the reactants.

From all above experiments using the unique vinyl stearate as the acyl donor, the reaction system and reaction conditions were identified for synthesis of saturated fatty acid N-acylethanolamines.

Example 8

Determining Reaction Conditions for the Synthesis of N-stearoyl and N-palmitoylethanolamine in Presence of Sodium Methoxide Catalyst The effects of sodium methoxide concentration, molar ratio of ethanolamine to fatty acid vinyl ester, temperature, and time on the amidation reaction were investigated. The results are shown in FIGS. 2-5. Data are expressed as means±standard deviations.

Figure 2A:
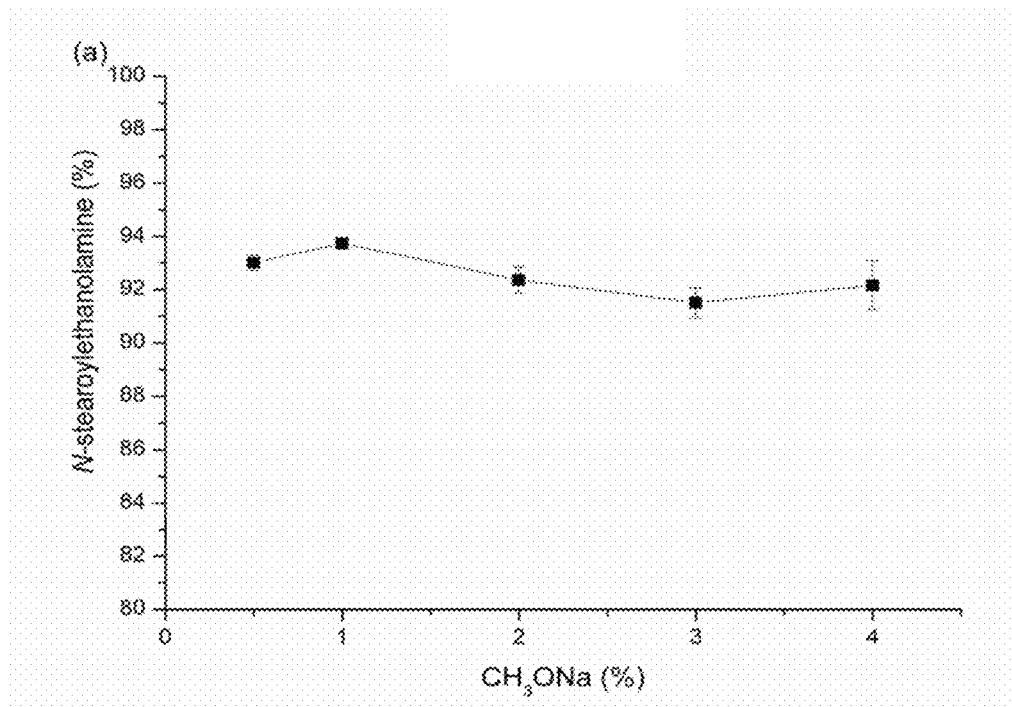
FIGS. 2A and 2B are graphs showing the effect of sodium methoxide concentration on the content of N-stearoyl (FIG. 2A) and N-palmitoylethanolamine (FIG. 2B) in the final amidation product.
Figure 2B:
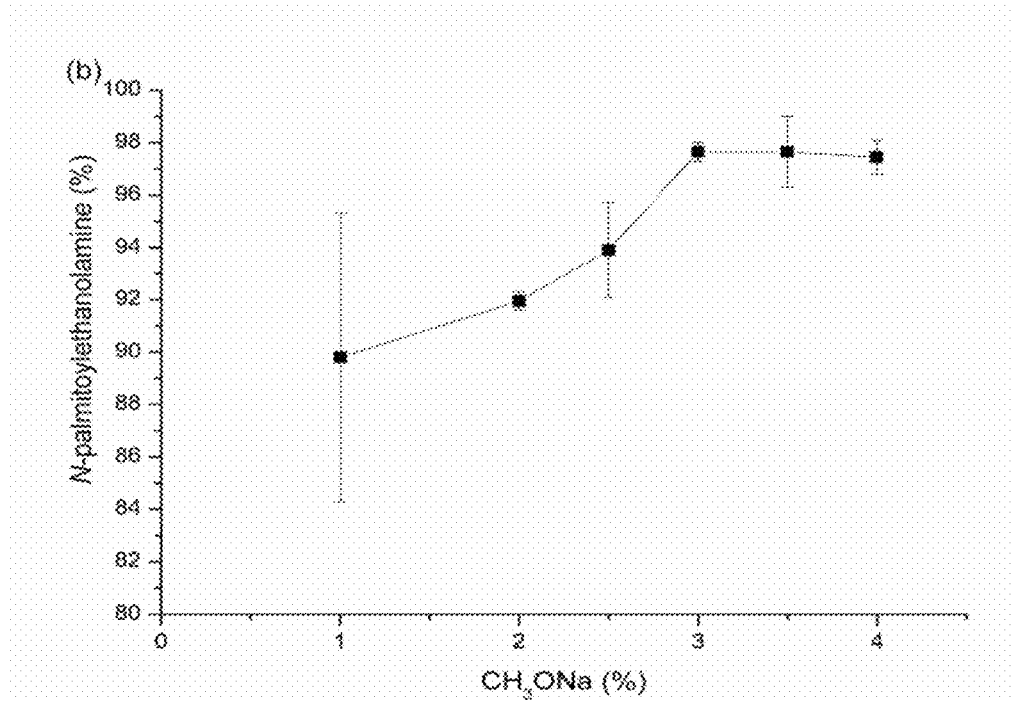

Regarding the concentration of sodium methoxide, the content of N-stearoylethanolamine formed at 0.5% catalyst was high but it tended to decrease slightly when the sodium methoxide was increased from 1-3% (FIG. 2). An explanation for the changes is that increase in the catalyst concentration may result in the formation of O-stearoylethanolamine produced by the esterification reaction (FIG. 6). Spontaneous acyl migration of O-stearoylethanolamine will happen, and thus the reaction typically proceeds towards amidation (Kanerva et al., *Acta. Chem. Scand.* 46:1101-05 (1992), which is hereby incorporated by reference in its entirety). In contrast, 3% sodium methoxide was determined for the synthesis of N-palmitoylethanolamine. In general, the amidation reaction is dominant.

Figure 3A:
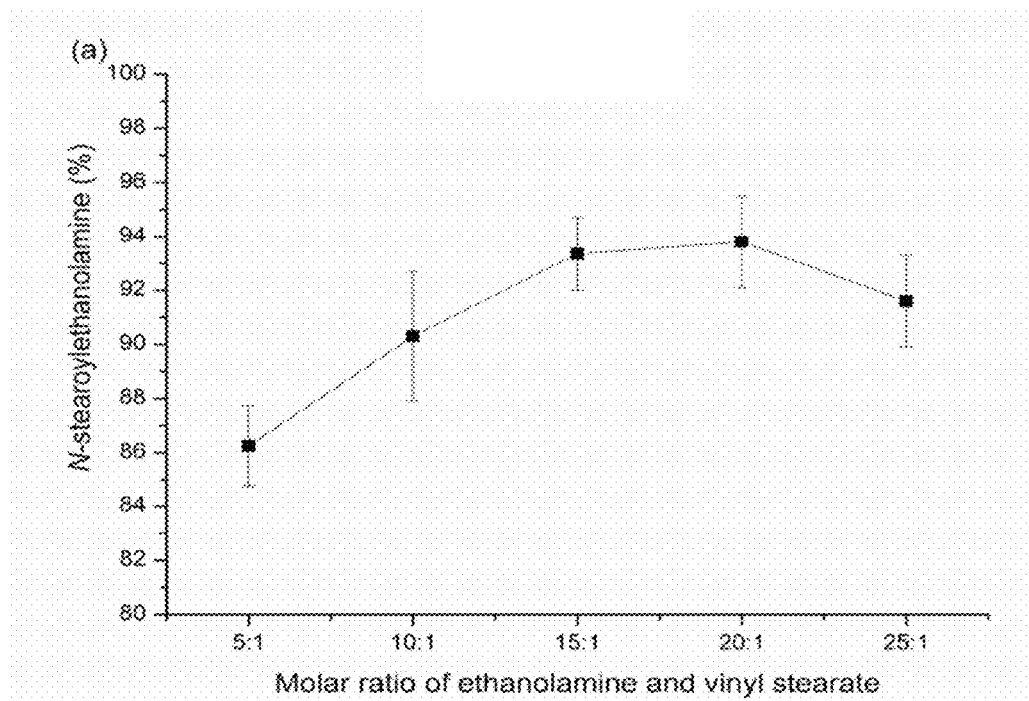
FIGS. 3A and 3B are graphs showing the effect of ethanolamine to vinyl ester fatty acid molar ratio on the content of N-stearoyl (FIG. 3A) and N-palmitoylethanolamine (FIG. 3B) in the final amidation product.
Figure 3B:
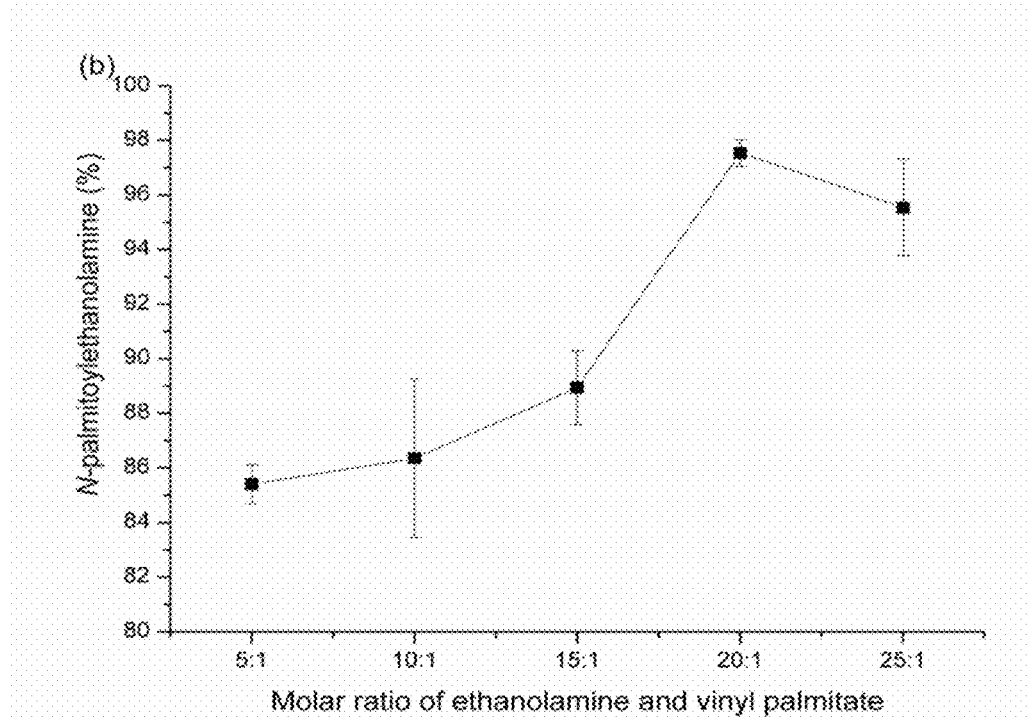

Responses of N-stearoyl and N-palmitoylethanolamine to molar ratio of ethanolamine to vinyl ester were similar. The content of N-acylethanolamines increased gradually with the increase of molar ratio from 5:1 to 20:1 (FIG. 3). Reactions with 5:1 and 10:1 ratios were incomplete because it was difficult to completely dissolve the final products at 60° C. The reason for the slight reduction in the content of N-acylethanolamine at the molar ratio above 20:1 is unknown. The 20:1 molar ratio was used as a better reaction condition.

Figure 4A:
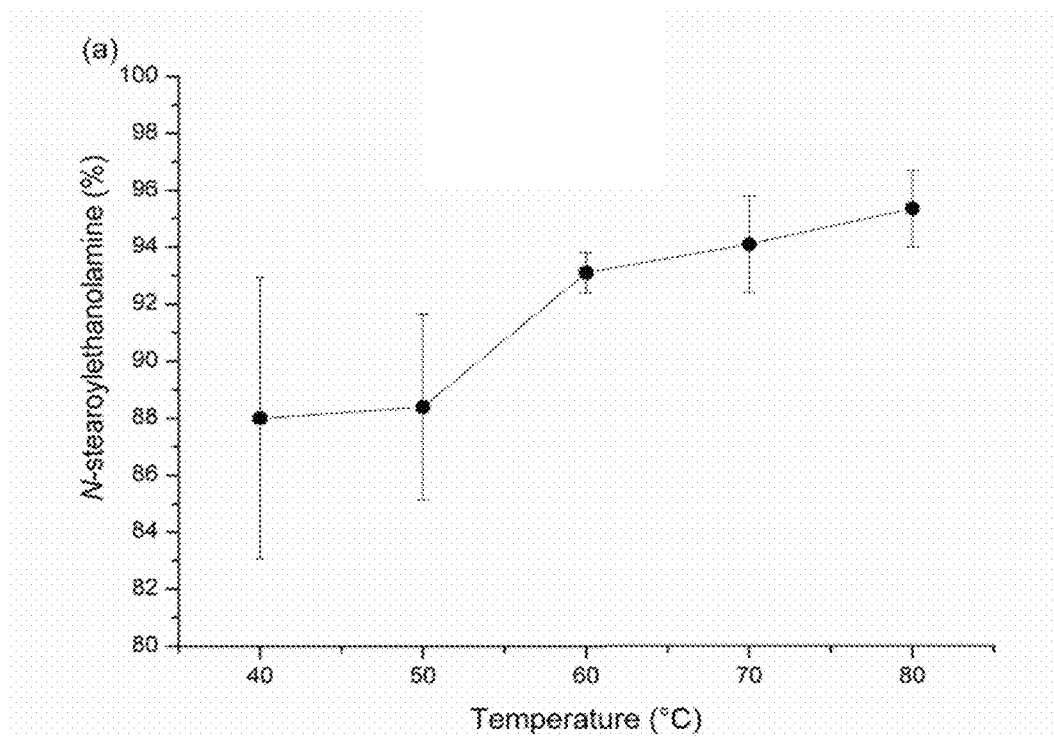
FIGS. 4A and 4B are graphs showing the effect of reaction temperature on the content of N-stearoyl (FIG. 4A) and N-palmitoylethanolamine (FIG. 4B) in the final amidation product.
Figure 4B:
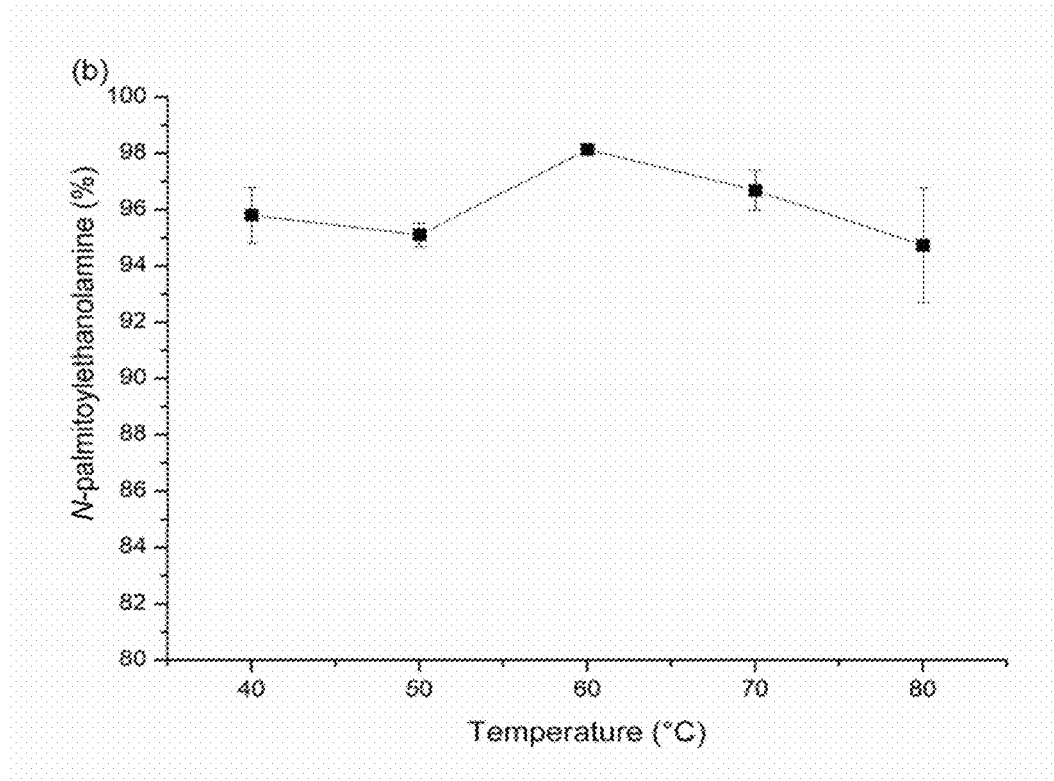
Figure 5A:
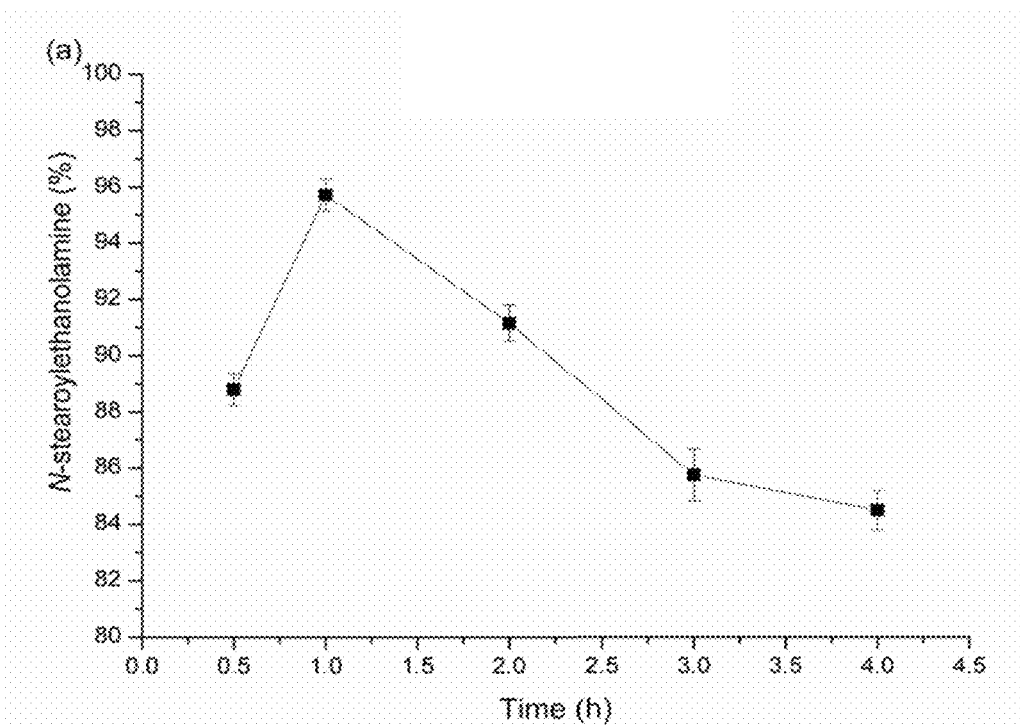
FIGS. 5A and 5B are graphs showing effect of reaction time on the content of N-stearoyl (FIG. 5A) and N-palmitoylethanolamine (FIG. 5B) in the final amidation product.
Figure 5B:
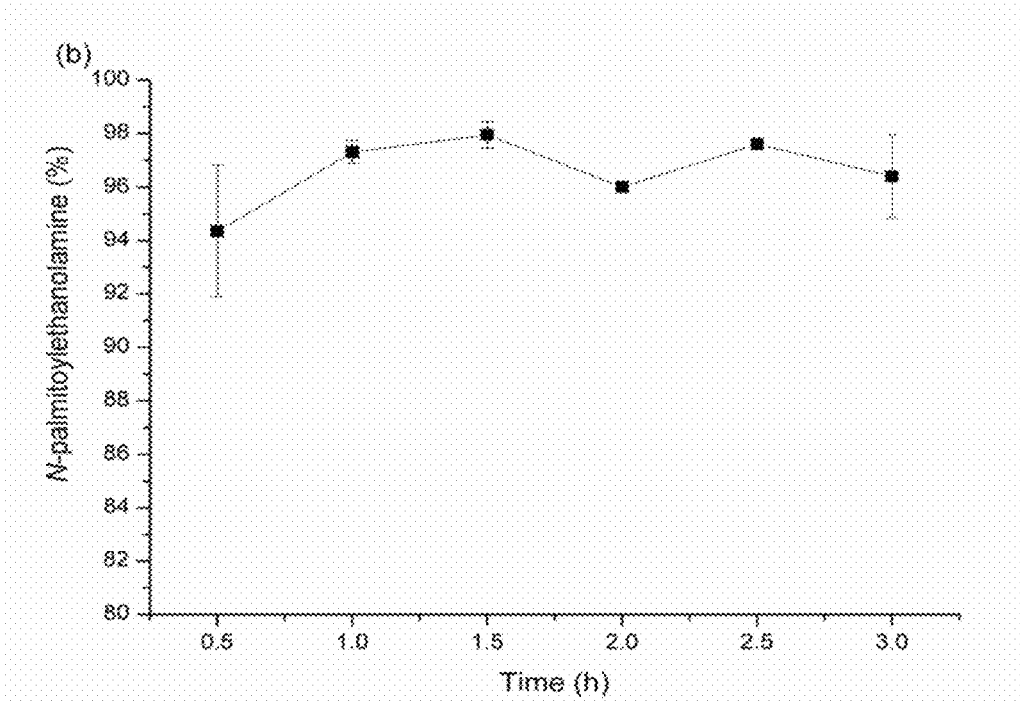

The reaction temperature was varied from 40° C. to 80° C. Results from FIG. 4A show that the increase of temperature was beneficial to the reaction, perhaps because of the increase in the rate of both amidation reaction and acyl migration, which resulted in more ester being converted to amide. The reaction at 80° C. resulted in the formation of 95.4% N-stearoylethanolamine. The color of product became dark if the temperature was increased further. Accordingly, 80° C. was selected as a better reaction temperature for the synthesis of N-stearoylethanolamine. However, the response of N-palmitoylethanolamine to temperature was different from that of the N-stearoylethanolamine, in that N-palmitoylethanolamine yield did not change as sharply with the changes in temperature. The content of N-palmitoylethanolamine seemed to have reached a maximum at 60° C. (FIG. 4B). The different reaction temperatures for these two N-acylethanolamines may be due to the difference in the sodium methoxide concentration used.

The content of N-stearoylethanolamine after 1-hour reaction was significantly higher than other time points (FIG. 5A), perhaps due to the side reactions if the reaction time was prolonged. In contrast, the reaction time did not seem to be a significant factor for the synthesis of N-palmitoylethanolamine. Accordingly, the 1-1.5 hour range was considered as better for the synthesis of N-stearoyl and N-palmitoylethanolamine.

After all above reaction parameters were examined, 1% sodium methoxide, 20:1 molar ratio of ethanolamine to vinyl stearate, 80° C., and 1 hour were used for the synthesis of N-stearoylethanolamine; and 3% sodium methoxide, 20:1 molar ratio of ethanolamine to vinyl palmitate, 60° C., and 1.5 hour were used for the synthesis of N-palmitoylethanolamine. The purity of N-stearoyl and N-palmitoylethanolamine was 95.7±0.6% and 98.0±0.5%, respectively, under these reaction conditions.

For a scaled-up synthesis, ethanolamine (600 mmol) was reacted with vinyl stearate or palmitate (30 mmol) using agitation under the reaction conditions determined above. There was 95.3% N-stearoylethanolamine and 96.5% N-palmitoylethanolamine in the final product after water washing.

Thin-layer chromatography (TLC) purity confirmation of the N-acylethanolamine was performed to show that there were no other lipids that may have been eluted from the gas chromatography (GC) column. The Retention Factors (Rf) values of N-stearoyl and N-palmitoylethanolamine were about 0.49-0.48, and the Rf values of the corresponding standards were all about 0.48. There was no other major lipid impurity except some very faint bands of residual fatty acyl vinyl esters or O-acylethanolamine.

Structural confirmation of N-acylethanolamine was performed by $^1$H NMR. Amide peak for —$CH_2CH_2CONH$— ($\delta$ 5.9, 1H) was observed, and no NMR peak of —$COOCH_2CH_2NH_2$ ($\delta$ 4.2-4.4, 2H) and —$COOCH_2CH_2NH_2$ ($\delta$ 1.1-1.5, 2H) were observed.

Discussions of Examples 1-8

Traditionally, synthesis of N-acylethanolamine had been performed with free fatty acid, fatty acid methyl ester, fatty acid chloride and triacylglycerol. In Examples 1-8, however, fatty acid vinyl ester was used as acyl donor to synthesize N-acylethanolamines. The possible reaction routes for acylation of ethanolamine with vinyl stearate are presented in FIG. 6.

Figure 7A:
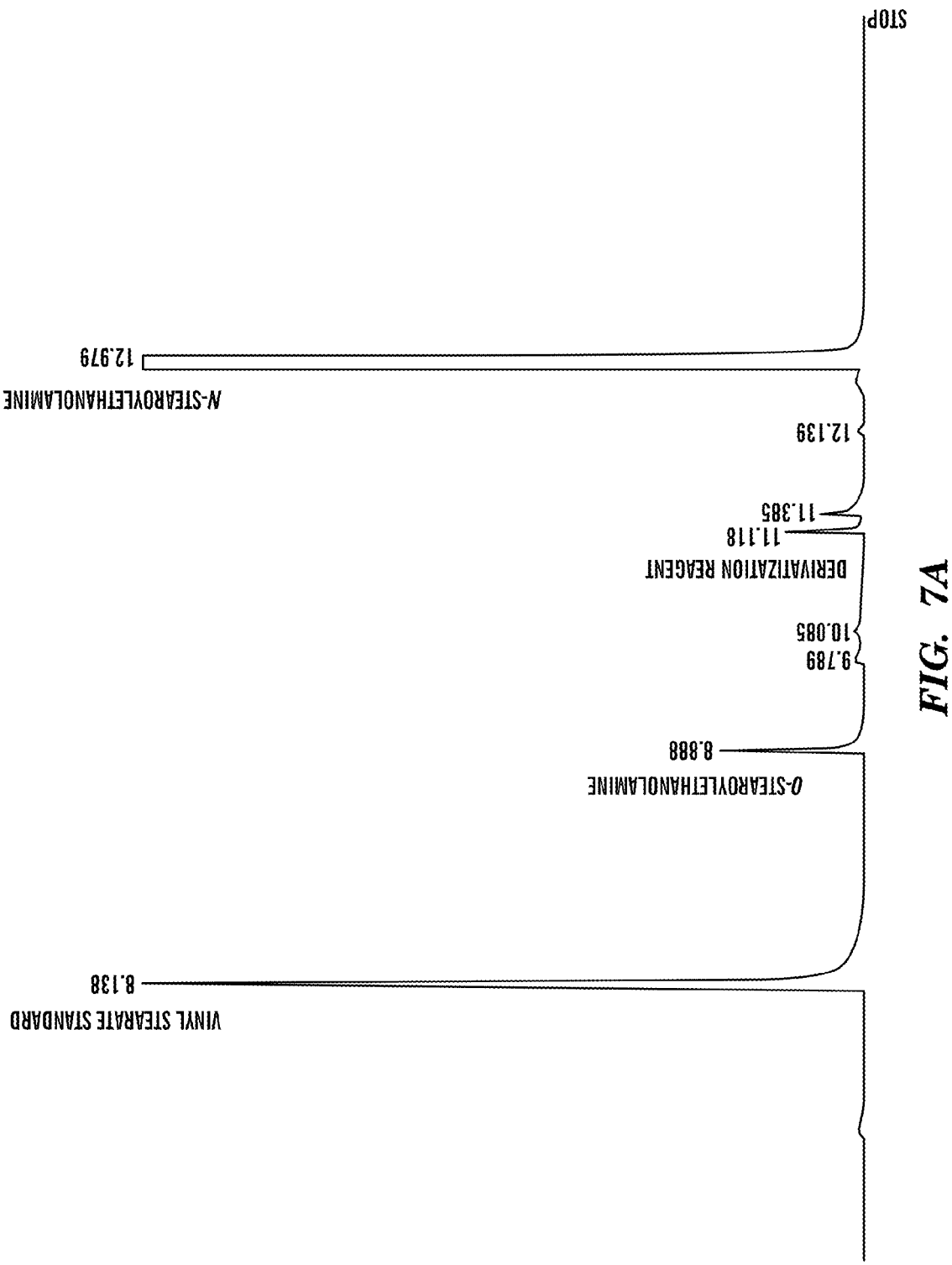
FIGS. 7A and 7B are GC chromatograms of N-palmitoyl (FIG. 7A) and N-stearoylethanolamine (FIG. 7B). Peaks of fatty acid vinyl ester standards and peaks from reaction products are superimposed for retention time comparison.
Figure 7B:
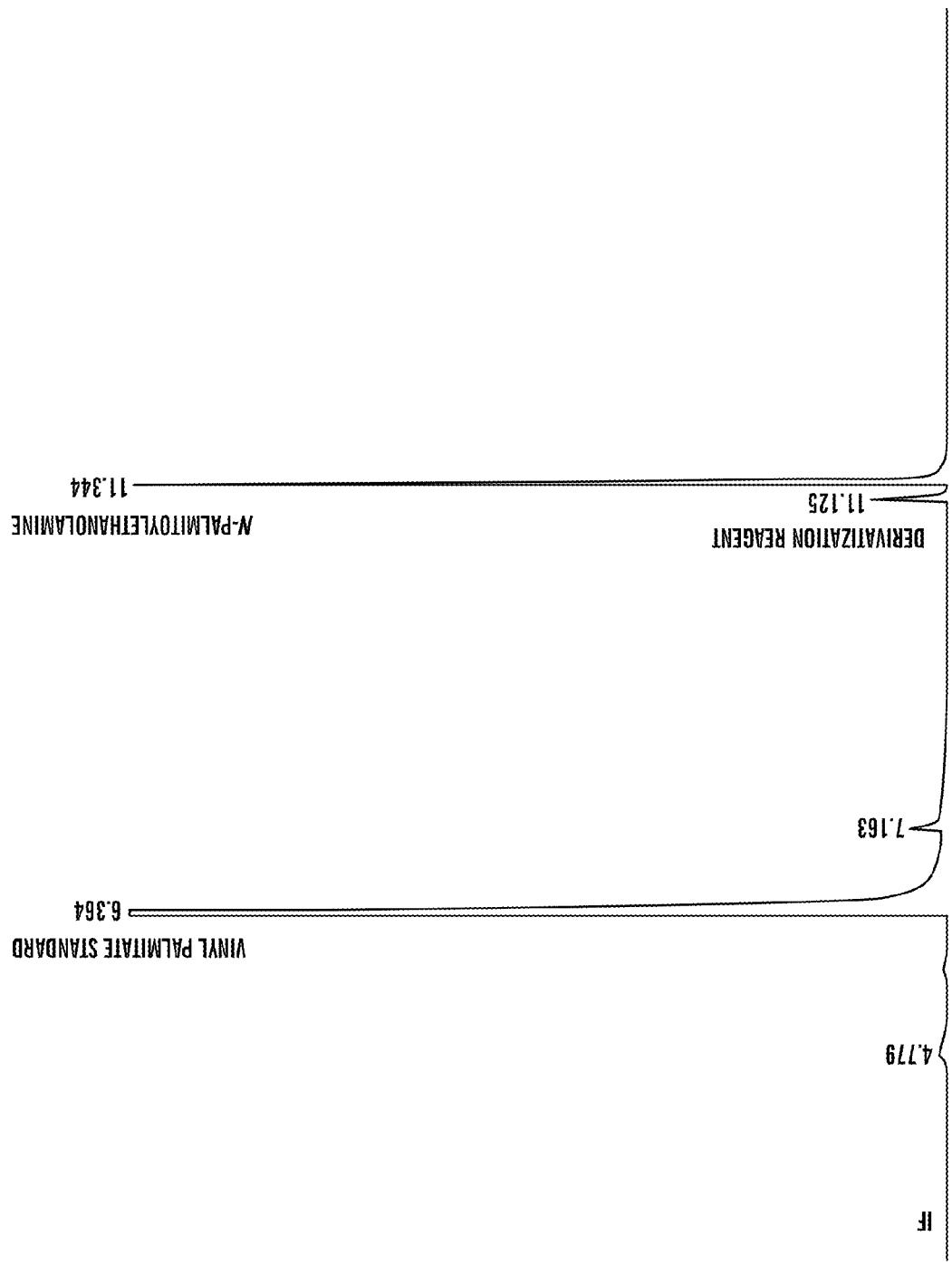

Three reactions might have occurred in the system. Amidation reaction was dominant and resulted in the formation of N-acylethanolamines and ethenol which tautomerized to a non-nucleophilic acetaldehyde immediately (Halldorsson et al., *Tetrahedron* 59:9101-09 (2003); Halldorsson et al., *Tetrahedron Lett.* 42:7675-77 (2001), which are hereby incorporated by reference in their entirety). Acetaldehyde (boiling point of 20.8° C.) could be evaporated at ambient temperature. The main side reaction product was O-acylethanolamine, resulting from esterification reaction between ethanolamine and fatty acid vinyl ester. However, spontaneous acyl migration would happen when a large amount of O-acylethanolamine was produced (Tufvesson et al., *Biotechnol. Bioeng.* 97:447-53 (2007), which is hereby incorporated by reference in its entirety). As the acyl migration step was too fast to be monitored, the reaction appeared to proceed via direct amidation when the conditions were suitable (Tufvesson et al., *Biotechnol. Bioeng.* 97:447-53 (2007); Kanerva et al., *Acta. Chem. Scand.* 46:1101-05 (1992), which are hereby incorporated by reference in their entirety). In the reaction system of Examples 1-8, the formation of N,O-bis-acylethanolamine was not favored due to the large excess of ethanolamine and it was not seen. Therefore, the impurities in the final product might have included ethanolamine (if not completely washed away by water), fatty acid vinyl ester, and O-acylethanolamine. Under the selected reaction conditions determined from Examples 1-8, almost all fatty acid vinyl ester was converted as verified by GC, while ethanolamine was removed by water washing. Thus, the impurity left was O-acylethanolamine, as shown in the GC chromatogram (FIG. 7B).

During the process of product purification, the non-polar acyl vinyl esters, N-acylethanolamines and O-acylethanolamine could not be removed by water wash and thus no loss of these compounds would occur. Therefore, the purity or percentage of N-acylethanolamines in the final lipid extract as determined by GC can be used as an indicator to monitor the amidation reaction, as described herein.

For GC product characterization, the peak at 11.1-11.2 minutes was attributed to the silylation reagent based on retention times determined by control injections. In addition, area of N-acylethanolamines increased proportionally to the sample amount used, whereas the area of the peak at 11.1-11.2 minutes remained almost constant even after the sample size was increase from 3 to 12 mg. This observation was also reported in O'Connell, *Anal. Chem.* 49:835-38 (1977), which is hereby incorporated by reference in its entirety. Peaks that had common retention times as the silylating reagent peak were not included for the purity calculation.

As reported in the literature, products with a N-acylethanolamine content ranging from 60% to 90% were obtained when free fatty acid (Liu et al., *J. Agric. Food. Chem.* 49:5761-64 (2001); Plastina et al., *Lett. Org. Chem.* 6:444-47 (2009), which are hereby incorporated by reference in their entirety), fatty acid methyl ester (Farris, *J. Am. Oil Chem. Soc.* 56:770-73 (1979), which is hereby incorporated by reference in its entirety) and triacylglycerol (Khanmohammadi et al., *J. Surfactants Deterg.* 12:37-41 (2009), which is hereby incorporated by reference in its entirety) were used as the acyl donor. A high temperature and long reaction time (100° C. for 6-12 hours) in the absence of a catalyst resulted in undesirable product quality. In a recent study, much milder reaction conditions were used for the synthesis. Plastina et al. (Plastina et al., *Lett. Org. Chem.* 6:444-47 (2009), which is hereby incorporated by reference in its entirety) used a free fatty acid to synthesize N-acylethanolamines at 40° C. for 6-15 hours in hexane with lipase (Novozym 435). However, a high concentration of lipase was shown to be essential for the reaction, which made the reaction uneconomical. The study from Plastina et al. did not show product purity, but did report a 80% yield after preparative LC purification. By comparison, the purity of N-stearoyl and N-palmitoylethanolamines in Examples 1-8 was approximately 96% and 98%, respectively, after the removal of the excess ethanolamine. Additionally, fatty acid vinyl ester was shown to be 100% converted when the reaction was performed at the reaction conditions determined in Examples 1-8, as none of these reactants were detected by GC.

The unique property of these reactions is its irreversibility. The amidation reaction between the free fatty acid, fatty acid methyl ester or triacylglycerol and ethanolamine is reversible. The yield of N-acylethanolamines might be increased by removal of water, methanol, or glycerol under reduced pressure; however, this was not desirable as the ethanolamine would also be evaporated due to its relatively low boiling point (170° C.) (Tufvesson et al., *Biotechnol. Bioeng.* 97:447-53 (2007), which is hereby incorporated by reference in its entirety). When fatty acid vinyl ester was used as the acyl donor, the amidation reaction was irreversible, because of the tautomerization of the by-product to a non-nucleophilic acetaldehyde. Acetaldehyde has a boiling point of 20.8° C., so it can be evaporated easily without the loss of ethanolamine. Thus, this irreversibility promoted the amidation reaction. Fatty acid vinyl esters were previously applied to the synthesis of symmetrical diacylglycerol and triacylglycerol (Halldorsson et al., *Tetrahedron* 59:9101-09 (2003); Andrews et al., *Tetrahedron* 64:9197-9202 (2008), which are hereby incorporated by reference in their entirety). However, they have not been used for N-acylethanolamine synthesis.

The amount of ethanolamine influenced the solubility of products, and it perhaps acted as a catalyst (Feairheller et al., *J. Am. Oil Chem. Soc.* 71:863-66 (1994); Kolancilar, *J. Am. Oil Chem. Soc.* 81:597-98 (2004); Bilyk et al., *J. Am. Oil Chem. Soc.* 69:488-91 (1992), which are hereby incorporated by reference in their entirety). Using ethanolamine as a solvent is economical, because this material is readily available and affordable ($50.4 per liter from the Sigma Chemical Company).

The reaction conditions for the amidation reaction determined from Examples 1-8 reduced the esterification and promoted the amidation reaction. It was shown in these examples that high temperatures were not desirable when vinyl stearate was used as the acyl donor as this might lead to the formation of unwanted color. No reaction occurred when the reaction was conducted at 45° C. in hexane with sodium methoxide or a low concentration of lipase. The use of an excess ethanolamine as the solvent proved effective for the synthesis of N-acylethanolamines. The experiments in Examples 1-8 established a new route for the synthesis of N-stearoyl and N-palmitoylethanolamines. The reaction was fast and the reaction conditions were mild. This reaction resulted in the formation of N-acylethanolamines with high purity (95%) after simply washing the product with water. These high-purity products can be used in biological activity evaluations.

Example 9

Experimental Materials

All chemicals were purchased from the Sigma Aldrich Chemical Company (St. Louis, Mo.) except the followings: Ethanolamine (>99%) was purchased from the Fisher Scientific (Fair Lawn, N.J.). *Candida Antarctica* (Novozym 435) lipase was provided by Novozymes (Blair, Nebr.).

Example 10

Purification of Oleic Acid

The commercial oleic acid product contained 89.6% oleic acid, 4.2% stearic acid and 6.2% linoleic acid. The purification process herein included two steps: removal of linoleic acid and followed by removal of stearic acid. Because linoleic acid can be well dissolved in methanol at −23° C. (BI: LIPID CHEMISTRY (Chemical Industry Press, Beijing, China, 2005), which is hereby incorporated by reference in its entirety), whereas oleic acid and saturated fatty acids can be crystallized from methanol, experiments were conducted to obtain pure oleic acid by low temperature crystallization. The commercial oleic acid product of 5 mL was mixed with 5, 10, 15, 20, 25 mL methanol at −23° C. for 4 hours to investigate the effect of solvent quantity on the purity and the yield of oleic acid.

Linoleic acid was removed by collecting the crystals by vacuum filtration in a cold room (about 5° C.) to fully remove the liquid phase.

In the second step, stearic acid was removed by placing the mixture (4:1 ratio of methanol to oleic acid) at −18° C. due to the lower solubility of stearic acid in methanol compared to oleic acid (BI: LIPID CHEMISTRY (Chemical Industry Press, Beijing, China, 2005), which is hereby incorporated by reference in its entirety). Once the crystal was observed in the solution, additional 15 minutes was allowed to fully crystallize the saturated fatty acid. The liquid phase was then collected by vacuum filtration in a cold room and crystal phase was discarded. All the above experiments were conducted in duplicate.

Purification of oleic acid was then conducted on a large scale. Two hundred milliliters of oleic acid was divided into two groups as two replicates. Methanol and oleic acid were mixed at −23° C. for 4 hours with 4:1 volume ratio to remove the linoleic acid as a first step and the crystal phase collected was mixed with methanol in 1:4 volume ratio at −18° C. to remove saturated fatty acid as a second step.

Example 11

Synthesis of Oleoyl Ethanolamide

Amidation of Ethanolamine with Oleic Acid in the Presence of an Excess Ethanolamine as Solvent The modified procedure of Kolancilar, *J. Am. Oil. Chem. Soc.* 81:597-98 (2004), which is hereby incorporated by reference in its entirety, in which an excess ethanolamine was used as a solvent, was followed. Oleic acid (1 mmol), ethanolamine (10 mmol), and 50% lipase (relative to total reactants) were placed in a 10-mL round bottom flask. The reaction was conducted under agitation at ambient temperature for 6 and 24 hours or conducted at 65° C. for 4, 8, and 20 hours. The reaction mixture was then washed with 5 mL distilled water at 6° C. for three times to remove the excess amount of ethanolamine. The lipase was removed by filtration. The oleoyl ethanolamide product was then derivatized and quantified by GC as described in the following examples.

Amidation of Ethanolamine with Oleic Acid in Hexane:

This experiment was carried out according to the procedure of using free fatty acid as acyl donor (Plastina et al., *Lett. Org. Chem.* 6:444-47 (2009), which is hereby incorporated by reference in its entirety). Ethanolamine (1 mmol) in hexane (1 mL) was mixed with oleic acid (1 mmol) in a 10-mL round bottom flask in the presence of the lipase (50%, relative to total reactants). The reaction was conducted with agitation at ambient temperature for 4, 8, and 24 hours or at 65° C. for 4, 8, and 20 hours before hexane was removed under reduced pressure.

These two methods for oleoyl ethanolamide synthesis were compared to determine reaction conditions for the synthesis.

Example 12

Determining Reaction Conditions for Oleoyl Ethanolamide Synthesis

The experimental setup is outlined in Table 4.

TABLE 4

Experimental setup for amidation reaction between oleic acid and ethanolamine[a]

| Level | $X_1$ (%) | $X_2$ (μL) | $X_3$ (mL) | $X_4$ (° C.) | $X_5$ (h) |
|---|---|---|---|---|---|
| 1 | 10 | 0 | 0.5 | 45 | 1 |
| 2 | 20 | 10 | 1.0 | 55 | 2 |
| 3 | 30 | 20 | 1.5 | 65 | 3 |
| 4 | 40 | 30 | 2.0 | 75 | 4 |
| 5 |    | 40 | 3.0 |    | 5 |

[a]$X_1$: Lipase. Reaction was conducted by reacting ethanolamine with oleic acid in 1 mL hexane without water. All reactions were conducted by reacting 1 mmol ethanolamine with 1 mmol oleic acid at 65° C. for 2 hours in 1.5 mL hexane and 10 μL water with 30% enzyme unless otherwise stated; $X_2$: Moisture content, conducted by reacting ethanolamine with oleic acid in 1 mL hexane; $X_3$: Hexane amount; $X_4$: Reaction temperature; $X_5$: Reaction time.

Effects of amount of lipase, hexane and water, reaction temperature and time as single factors on the purity of oleoyl ethanolamide were investigated while other reaction conditions were fixed.

Effect of Enzyme Concentration:

The amount of enzyme was investigated by reacting ethanolamine (1 mmol) with oleic acid (1 mmol) at 65° C. for 2 hours in 1 mL hexane with 10, 20, 30, and 40% lipase and without the use of water.

Effect of Moisture Content:

The moisture content was investigated by reacting ethanolamine (1 mmol) with oleic acid (1 mmol) at 65° C. for 2 hours in 1 mL hexane with 30% lipase. Water was added in the reaction mixture at 0, 10, 20, 30, and 40 μL (0, 2.8, 5.6, 8.4, 11.2%, relative to total reaction mixture).

Effect of Hexane Quantity:

The amount of hexane was investigated by reacting ethanolamine (1 mmol) with oleic acid (1 mmol) at 65° C. for 2 hours in 0.5, 1, 1.5, 2, or 3 mL hexane with 30% lipase and 10 μL water.

Effect of Reaction Temperature:

The reaction temperature was investigated by reacting ethanolamine and oleic acid at equal molar ratio (1 mmol), under agitation at 45, 55, 65, and 75° C. for 2 hours in 1.5 mL hexane and 10 μL water with 30% lipase.

Effect of Reaction Time:

The reaction time was investigated by equal molar ratio (1 mmol) ethanolamine and oleic acid were mixed at 65° C. in 1.5 mL hexane and 104, water with 30% lipase in 1 hour to 5 hours range.

Synthesis of Oleoyl Ethanolamide on a Large Scale

The reaction conditions used were exactly the same as the reaction conditions established on 1 mmol scale. Ethanolamine (50 mmol) and oleic acid (50 mmol) were mixed at 65° C. for 6 hours in 75 mL hexane with 30% lipase and 0.5 mL water. Hexane of 150 mL was then added to the system after lipase was removed by filtration. The mixture was placed at 6° C. for 1 hour to crystallize oleoyl ethanolamide from hexane.

All the above experiments were conducted in duplicate and the results were expressed as means±standard deviations.

Example 13

Procedures for Preparing Methyl Esters of Fatty Acids and Oleoyl Ethanolamide Derivative One drop oleic acid of commercial or purified product was mixed with 14% boron trifluoride-methanol solution in 5 mL glass vial at 70° C. for 5 minutes. 2 mL hexane was then added to the reaction mixture to extract the fatty acid methyl esters. The anhydrous reaction product of the oleoyl ethanolamide (about 5 mg) was placed into 2 ml, glass vial for producing its ether derivative for GC quantification. Pyridine (0.5 mL) was added followed by hexamethyldisilazane (0.15 mL) and trimethylchlorosilane (0.05 mL). The mixture was shaken for 15-30 seconds and allowed to stand for 1 hour or stored in a freezer (0° C.) overnight to allow the upper layer phase turn clear (Wood et al., *J. Am. Oil. Chem. Soc.* 42:161-65 (1965), which is hereby incorporated by reference in its enirety). GC was used to quantify oleoyl ethanolamide. The purity of oleoyl ethanolamide was calculated according to the peak area ratio.

Derivatives of fatty acids and oleoyl ethanolamide were quantified by an HP 5890 Series II capillary GC (Hewlett-Packard, PA) equipped with a flame ionization detector (FID) and using a 30 m×0.25 mm×0.25 μm (length×I.D.×film thickness) fused silica bonded phase capillary column SP-1 (Supelco, Bellefonte, Pa.). The carrier gas (helium) flow rate was 32.3 mL/min, and the split ratio was 7. The oven temperature for oleic acid quantification was programmed from 140° C. to 230° C. at a rate of 5° C./min, then programmed from 140° C.

to 300° C. at a rate of 10° C./min, and then held at 300° C. for 5 minutes for oleoyl ethanolamide quantification. The injector and detector temperatures were set to 250° C. for fatty acid analysis and 300° C. for oleoyl ethanolamide quantification.

Example 14

NMR Analysis for Structure Confirmation $^1$H-NMR qualitative analysis of the oleoyl ethanolamide product was conducted by using a Varian MR-400 Spectrometer (Foster City, Calif., USA) with $CDCl_3$ as solvent and TMS as the internal standard (chemical shift of 0 ppm).

Example 15

Statistical Analysis

All data were analyzed by one-way analysis of variance (ANOVA). Differences among the means were compared at P=0.05 using the Tukey's test. Different letters labeled in the figures (e.g., FIGS. 8, and 11-15) indicate significant differences for the specific quality parameter.

Example 16

Purification of Oleic Acid

The solubility of oleic acid at −20° C. is 4.02 g oleic acid/100 g methanol, compared to 233 g linoleic acid/100 g methanol. The solubility of stearic acid at −20° C. is 0.011 g/100 g methanol (BI: LIPID CHEMISTRY (Chemical Industry Press, Beijing, China, 2005), which is hereby incorporated by reference in its entirety). Thus, if methanol and the commercial oleic acid are mixed at −23° C., oleic acid and stearic acid can crystallize from methanol, while linoleic acid remains dissolved in methanol. If methanol and the partially purified oleic acid are mixed at −18° C., stearic acid can crystallize from methanol very fast, while oleic acid can remain relatively soluble in the methanol during a short crystallization time. Thus, stearic acid can be removed by collecting the liquid phase.

Figure 8:
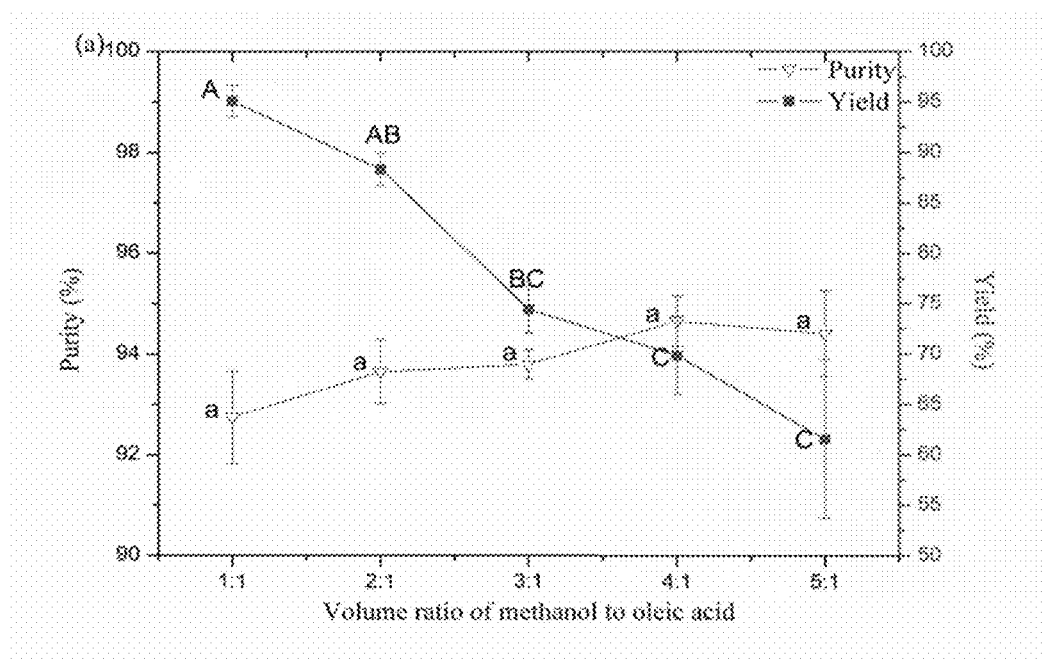
FIG. 8 is a graph showing the effects of volume ratio of methanol to oleic acid on the purity and yield of oleic acid after the removal of linoleic acid. The different letters on each individual curve indicate significant difference at $P=0.05$.

For the removal of linoleic acid, the effect of volume ratio of methanol to oleic acid on the purity and yield of oleic acid is shown in the FIG. 8. Crystallization conducted with 4:1 volume ratio for 4 hours resulted in removal of most linoleic acid. The purity was not significantly affected by the amount of solvent used. However, the larger the volume of solvent was used, the more the lipid was lost in the solvent. By this first purification step, the purity of oleic acid was increased from 89.6% to 94.7%, and linoleic acid and stearic acid were reduced from 6.2% to 1.9% and 4.2% to 3.4%, respectively. For a further purification step, a low temperature of −18° C. was effective to quickly separate the stearic acid crystals from methanol, affording 96.7±0.8% oleic acid with 62.2±5.4% overall yield. Linoleic and stearic acids were at 2.1% and 1.2% in the final product, respectively.

For the purification of oleic acid on a large scale (100 mL), the final purity and yield were 97.0±0.4% and 59.7±1.8%. This result shows an excellent feasibility and effectiveness of the crystallization purification process.

Example 17

Selecting Reaction Systems for the Oleoyl Ethanolamide Synthesis

The previous reactions conducted for the synthesis of fatty acid ethanolamide typically result in the formation of undesirable color and odor even though the addition of deodorizers and anti-oxidants has been suggested to improve the product quality (Kolancilar, J. Am. Oil. Chem. Soc. 81:597-98 (2004); Bilyk et al., J. Am. Oil. Chem. Soc. 69:488-91 (1992); Tufvesson et al., Biotechnol. Bioeng. 97:447-53 (2007), which are hereby incorporated by reference in their entirety). In this example, the feasibility of synthesizing oleoyl ethanolamide with a lipase by using an excess ethanolamine as a solvent and hexane as a solvent was compared. Using an excess ethanolamine as a solvent was shown to be effective for the synthesis of fatty acid ethanolamide when triacylglycerol was used as the acyl donor (Kolancilar, J. Am. Oil. Chem. Soc. 81:597-98 (2004); Bilyk et al., J. Am. Oil. Chem. Soc. 69:488-91 (1992), which are hereby incorporated by reference in their entirety).

The comparisons of using different solvents for the amidation reaction are shown in Tables 5 and 6.

TABLE 5

Synthesis of oleoyl ethanolamide with an excess (10x) ethanolamine as solvent

| | Temperature (° C.) | | | | |
|---|---|---|---|---|---|
| | Ambient | | | 60° C. | |
| | Time (h) | | | | |
| | 6 | 24 | 4 | 8 | 20 |
| Oleic acid (%) | 67.2 | 65.1 | 57.2 | 61.5 | 58.8 |
| Oleoyl ethanolamide (%) | 23.1 | 29.6 | 39.4 | 37.4 | 40.1 |

TABLE 6

Synthesis of oleoyl ethanolamide with hexane as solvent

| | Temperature (° C.) | | | | |
|---|---|---|---|---|---|
| | Ambient | | | 60° C. | |
| | Time (h) | | | | |
| | 4 | 8 | 24 | 4 | 8 | 20 |
| Oleic acid (%) | 51.8 | 43.3 | 28.5 | 0 | 0 | 0 |
| Oleoyl ethanolamide (%) | 45.5 | 54.1 | 69.9 | 96.8 | 94.5 | 93.2 |

In this example, less than 40% oleoyl ethanolamide was produced when the reactions were conducted with 50% lipase at ambient temperature for 24 hours or 60° C. for 20 hours in the presence of a large excess of ethanolamine. Increasing the reaction temperature was more effective than increasing time in improving the oleoyl ethanolamide content in the final mixture. The low purity of oleoyl ethanolamide was due to low conversion of oleic acid (Table 5).

Figure 10:
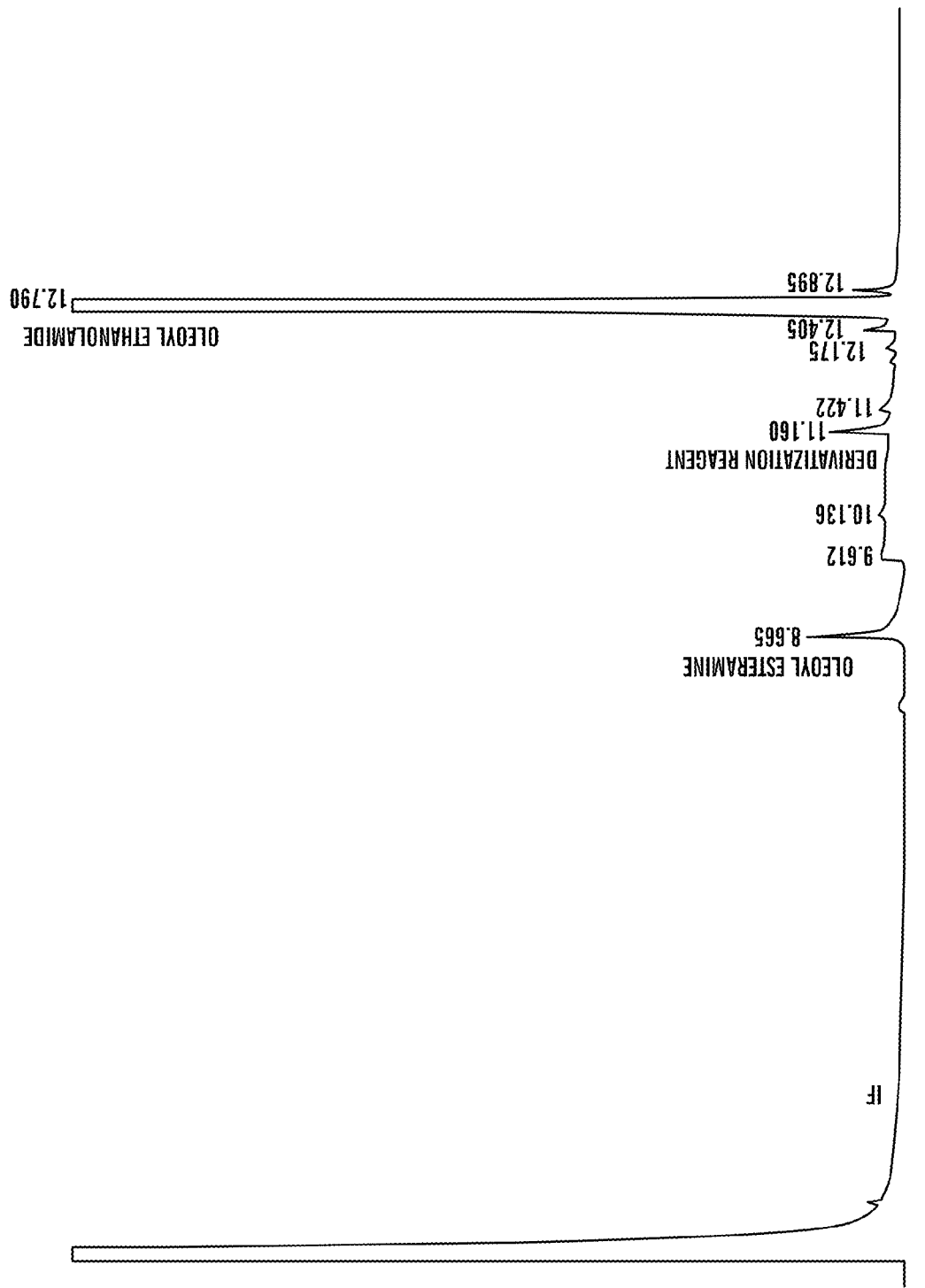
FIG. 10 is a GC chromatogram resulting from synthesis of oleoyl ethanolamide.

In comparison, when hexane was used as a solvent to synthesize oleoyl ethanolamide at ambient temperature for 24 hours, 69.9% oleoyl ethanolamide was obtained. When the reaction temperature was increased to 60° C., 96.8% oleoyl ethanolamide was produced in the system in only 4 hours and almost 100% oleic acid was converted (Table 6). The impurities in the final reaction mixture are perhaps from side reactions as shown in FIG. 9 and the formation of an esteramine as shown in a GC chromatogram (FIG. 10). The presence of esteramine in such a reaction mixture was also suggested by others (Tufvesson et al., Biotechnol. Bioeng. 97:447-53 (2007), which is hereby incorporated by reference in its entirety). Thus, the hexane system was used to synthesize oleoyl ethanolamide in the following examples.

GC was employed to measure oleoyl ethanolamide derivatives. Peak at 11.1-11.2 minutes (FIG. 10) was contributed by the silylation reagent rather than the sample as this peak also can be observed when only the silylation reagent was injected into GC. This observation has been reported by other researcher (O'Connell, *Anal. Chem.* 49:835-38 (1977), which is hereby incorporated by reference in its entirety).

$^1$H-NMR spectroscopy of oleoyl ethanolamide shows the following: δ 0.88 (t, 3H, CH$_3$), 1.26 (t, 20H, 10×CH$_2$), 1.63 (t, 2H, CH$_2$CH$_2$CONH), 2.01 (m, 4H, CH$_2$CH=CHCH$_2$), 2.20 (t, 2H, CH$_2$CH$_2$CONH), 3.43 (p, 2H, HOCH$_2$CH$_2$NH), 3.72 (t, 2H, HOCH$_2$CH$_2$NH), 5.34 (t, 2H, CH$_2$CH=CHCH$_2$), 5.9 (s, 1H, CH$_2$CH$_2$CONH). No $^1$H-NMR peak of —COOCH$_2$CH$_2$NH$_2$ (δ 4.2-4.4, 2H) and —COOCH$_2$CH$_2$NH$_2$ (δ 1.1-1.5, 2H) can be observed. Thus, the structure and purity of oleoyl ethanolamide were confirmed.

Example 18

Determining Reaction Conditions for the Oleoyl Ethanolamide Synthesis

The reaction conditions of the oleoyl ethanolamide synthesis were analyzed to decrease the esterification and promote the amidation reaction. The possible reaction routes for amidation of ethanolamine with oleic acid are presented in FIG. 9. Three reactions may occur in the system. The amidation reaction was predominant, and it resulted in the formation of oleoyl ethanolamide and water. The purity of oleoyl ethanolamide may be improved by removing water by vacuum; however, the high volatility of ethanolamine can be problematic (boiling point of 170° C.) (Tufvesson et al., *Biotechnol. Bioeng.* 97:447-53 (2007), which is hereby incorporated by reference in its entirety). The main side reaction product may be esteramine, resulting from an equal molar esterification reaction between ethanolamine and oleic acid. In general, spontaneous acyl migration can happen when a high concentration of esteramine is produced (Tufvesson et al., *Biotechnol. Bioeng.* 97:447-53 (2007); Kanerva et al., *Acta Chem. Scand.* 46:1101-05 (1992), which are hereby incorporated by reference in their entirety). Because the acyl migration step was very fast, the reaction appeared to proceed via direct amidation. The formation of esteramide was not favored due to the limited amount of free fatty acid in the reaction system. Therefore, the impurities in the final product may include ethanolamine, oleic acid, and esteramine. Under desired reaction conditions, almost all oleic acid and ethanolamine were converted. Thus, the main impurity is fatty acid esteramine as shown in the GC chromatogram (FIG. 10).

Figure 11:
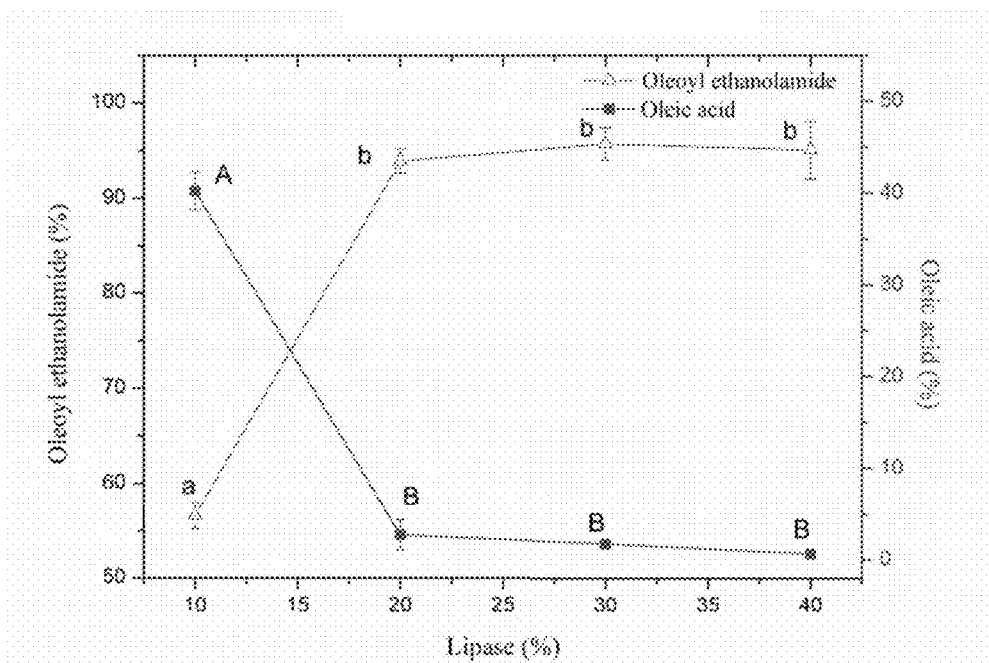
FIG. 11 is a graph showing the effect of Novozym 435 lipase concentration on the content of oleoyl ethanolamide and oleic acid in the final amidation product. The different letters on each individual curve indicate significant difference at $P=0.05$.

The results for optimization of oleoyl ethanolamide synthesis are presented in FIGS. 11-15. FIG. 11 shows the effect of lipase concentration on the conversion of oleic acid. The content of oleoyl ethanolamide was increased and oleic acid was decreased dramatically when lipase was increased from 10% to 20% (relative to total reactants). Even though 30% lipase did not give significantly higher conversion than that of 20%, 30% lipase was used to ensure a complete reaction.

Figure 12:
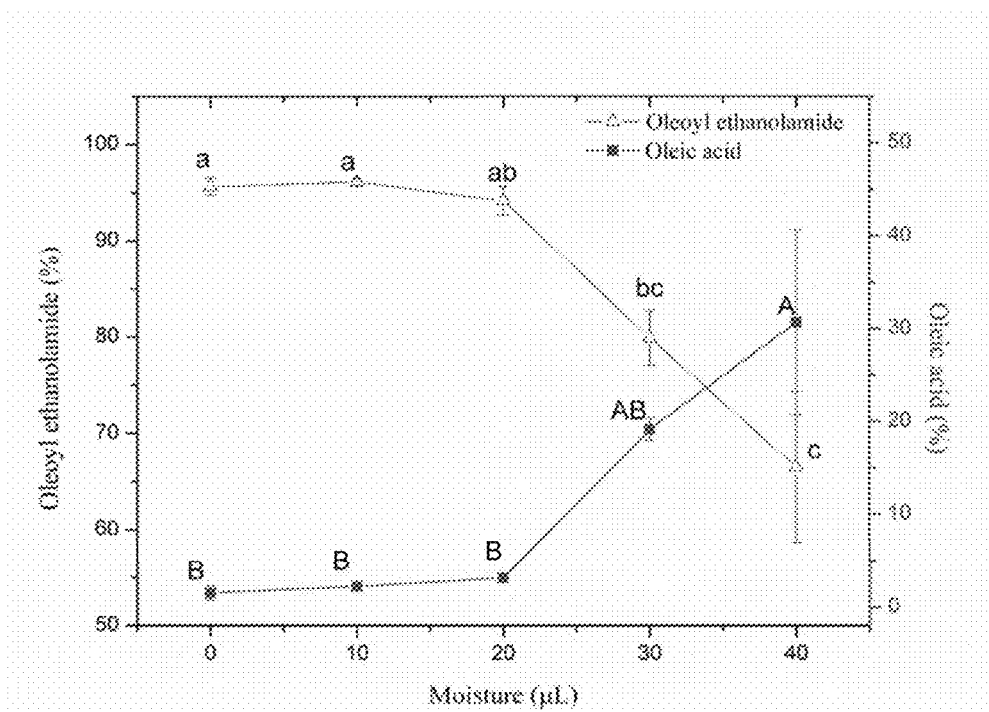
FIG. 12 is a graph showing the effect of moisture on the content of oleoyl ethanolamide and oleic acid in the final amidation product. The different letters on each individual curve indicate significant difference at $P=0.05$.

Moisture content was then investigated as it affects enzyme activity. Oleoyl ethanolamide content decreased significantly when the moisture content was increased from 20 μL to 40 μL (FIG. 12). The low oleoyl ethanolamide content was a result of low oleic acid conversion due to the reaction equilibrium. No significant differences in oleoyl ethanolamide and oleic acid content were observed between 0 and 20 μL water addition. In general, enzyme needs 0 to 5% moisture content for catalytic activity (Irimescu et al., *J. Am. Oil. Chem. Soc.* 78:65-70 (2001), which is hereby incorporated by reference in its entirety). In this example, 10 μL water (2.8%) was determined to be an appropriate condition. In this reaction, 18 μL water was produced if oleic acid and ethanolamine was fully reacted; thus, this water may also contribute to the moisture that is needed for enzyme activity. The moisture content of the enzyme itself was measured to be 1.56%. Based on how much enzyme was used (30%) in the 1 mmol reaction system, a total of 1.6 mg water was contained in the enzyme. This is relatively a small contribution, considering that 10 mg water was added (as an optimum) to the system and the 18 mg water was produced from the amidation reaction.

Figure 13:
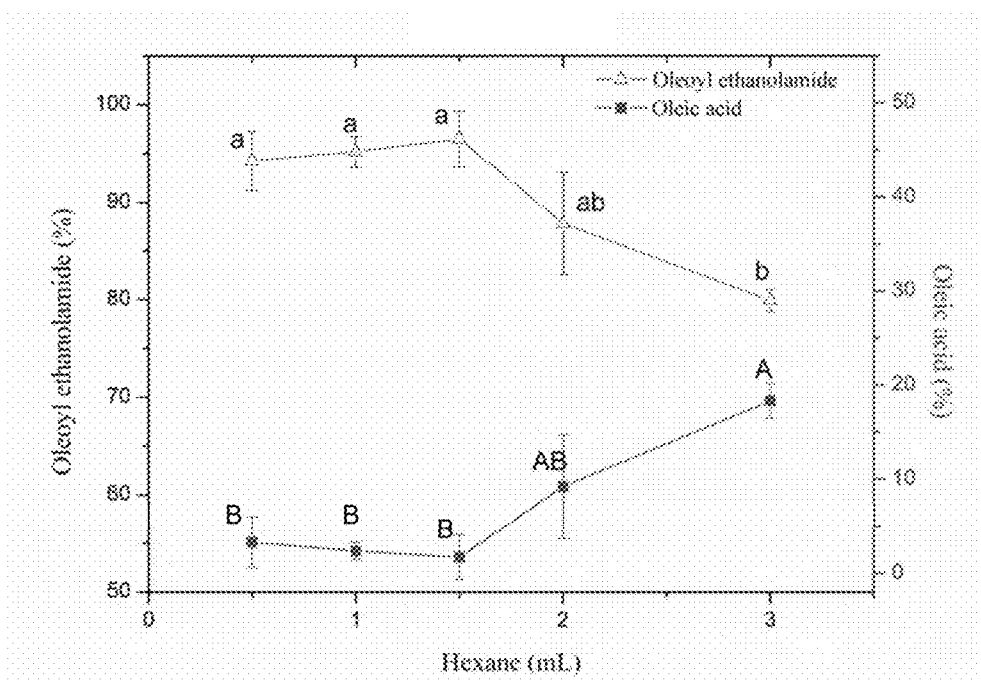
FIG. 13 is a graph showing the effect of hexane on the content of oleoyl ethanolamide and oleic acid in the final amidation product. The different letters on each individual curve indicate significant difference at $P=0.05$.

The amount of hexane was investigated, because solvent affects the solubility or dispersibility of the final product and concentrations of the enzyme and reactants. Low hexane amount results in low product solubility, while high hexane amount dilutes the enzyme and reactants which may affect the reaction negatively. FIG. 13 shows that the oleoyl ethanolamide content had a slight increase trend in the presence of 0.5 to 1.5 mL hexane, but decreased dramatically when more hexane was used. The reaction conducted in the presence of 1.5 mL hexane as solvent resulted in a high purity of oleoyl ethanolamide. Thus, 1.5 mL hexane was used when 1 mmol of each of the reactants was used.

Figure 14:
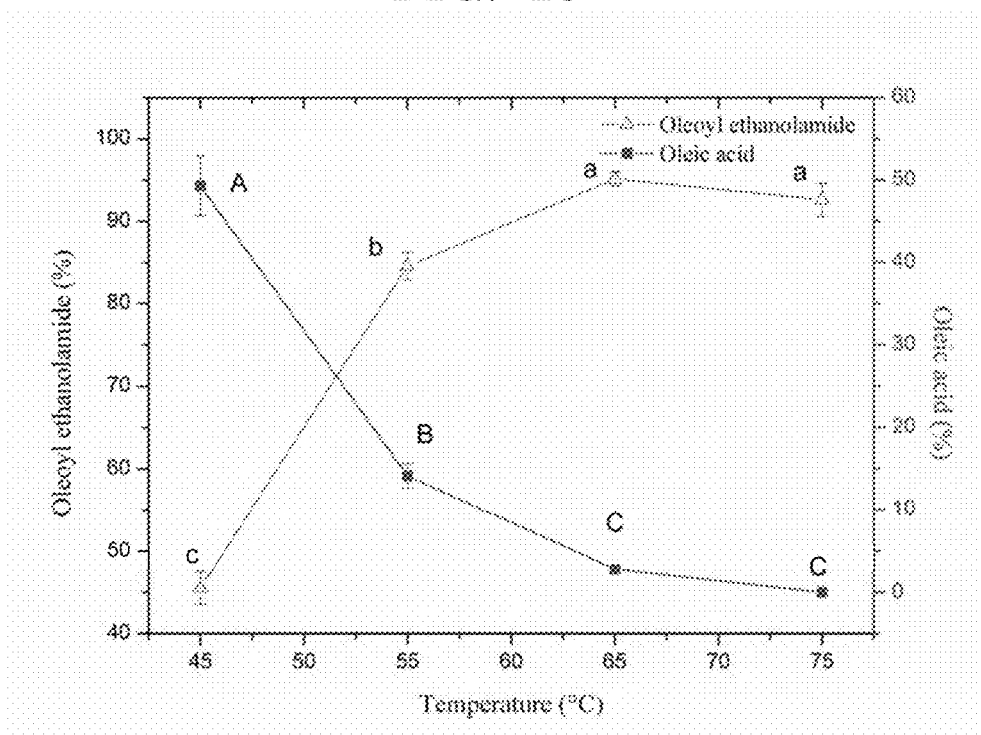
FIG. 14 is a graph showing the effect of reaction temperature on the content of oleoyl ethanolamide and oleic acid in the final amidation product. The different letters on each individual curve indicate significant difference at $P=0.05$.
Figure 15:
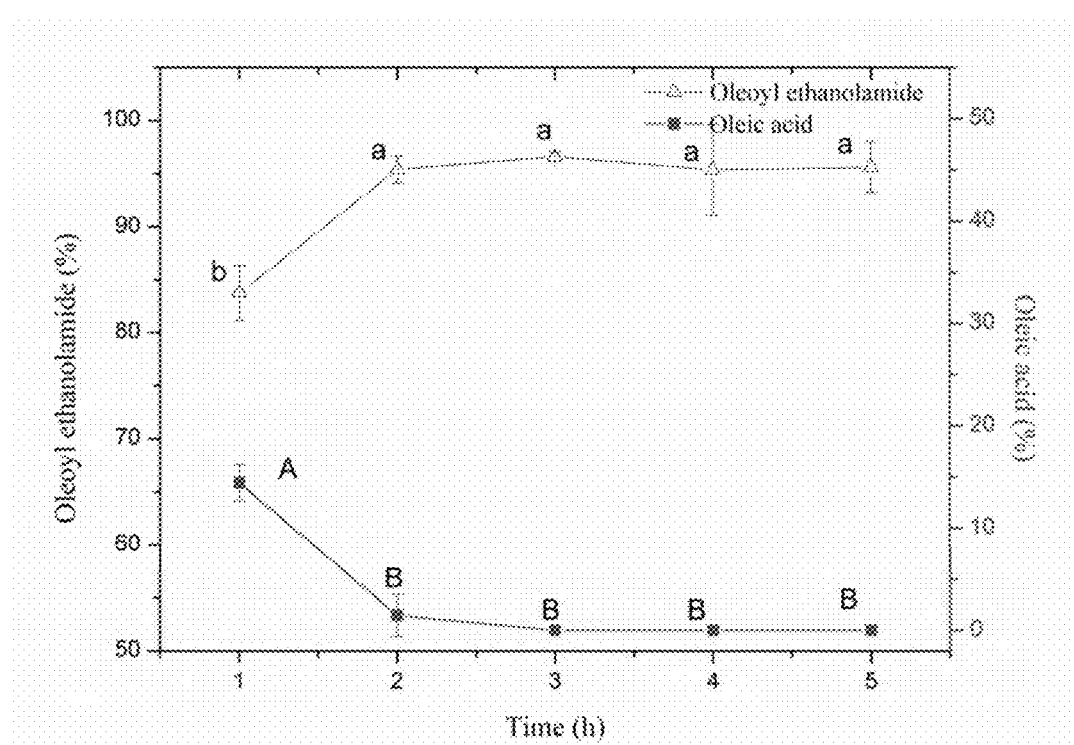
FIG. 15 is a graph showing the effect of reaction time on the content of oleoyl ethanolamide and oleic acid in the final amidation product. The different letters on each individual curve indicate significant difference at $P=0.05$.

Reaction temperature affects reaction rate, enzyme activity and solubility of oleoyl ethanolamide product. The maximal oleoyl ethanolamide content was observed at 65° C. with 30% lipase in 1.5 mL hexane and 10 μL water (FIG. 14). Accordingly, 65° C. was use as the reaction temperature.

The reaction time from 2 to 5 hours did not affect the content of oleoyl ethanolamide and oleic acid significantly. The maximum content of oleoyl ethanolamide was observed at 2 or 3 hours, during which time almost 100% oleic acid was converted. Thus, when 1 mmol oleic acid and 1 mmol ethanolamine were mixed at 65° C. for 3 hours with 30% lipase in 1.5 mL hexane and 10 μL, water, the purity of oleoyl ethanolamide was 96.6±0.4% and all oleic acid was consumed. This is an exceptional conversion reaction catalyzed by an enzyme.

Effects of various reaction conditions as a single factor on the purity of oleoyl ethanolamide were investigated while other reaction conditions were fixed. Interactions among these factors may exist. The optimal reaction condition may be different if a is used to generate a prediction model. However, certain concerns and limitations of using multi-factor response surface experimental design may exist (Dijkstra, *Eur. J. Lipid Sci. Technol.* 112:1290-93 (2010), which is hereby incorporated by reference in its entirety).

The application of the reaction conditions identified in Examples 9-18 on a small scale (1 mmol reactants) did not directly produce the similar purity for a large-scale synthesis. When 50 mmol ethanolamine was reacted with 50 mmol oleic acid at 65° C. for 6 hours with 30% lipase in presence of 75 mL hexane and 0.5 mL water, the final purity of oleoyl ethanolamide was about 79%, which was much lower than the purity of the small-scale synthesis with the same reaction conditions. After the enzyme was removed by filtration and the product was purified by crystallization at 6° C. for 1 hour in 150 mL hexane, the purity and yield of oleoyl ethanolamide in the crystallized product were 96.1±0.6% and 73.5±3.7%, respectively. The residual oleic acid was completely removed after crystallization. This is an example that a further purification step can be used to obtain high-purity oleoyl ethanolamide product when synthesis is on a larger reaction scale.

Discussions of Examples 9-18

Most of the earlier reports focused on the synthesis of saturated fatty acid alkanolamides; synthesis of unsaturated fatty acid alkanolamides with enzymes has received little attention. Purity of commercial alkanolamides for surfactant purpose that was synthesized by reacting ethanolamine with free fatty acid at high temperature (100-180° C.) (Maag, *J. Am. Oil. Chem. Soc.* 61:259-67 (1984), which is hereby incorporated by reference in its entirety) was low (about 80%) (Khanmohammadi et al., *J. Surfact. Deterg.* 12:37-41 (2009), which is hereby incorporated by reference in its entirety), and the product was of undesirable color and odor quality. In addition, oleic acid and oleoyl ethanolamide may be oxidized at such a high temperature range.

Tufvesson et al., *Biotechnol. Bioeng.* 97:447-53 (2007), which is hereby incorporated by reference in its entirety established a method for synthesis of lauroyl ethanolamide (melting point of 89° C.) by using the Novozym 435 lipase to catalyze the amidation reaction at a milder temperature (90° C.) in a solvent-free system. The final purity of lauroyl ethanolamide in their reaction mixture was 95% with 97% conversion. In contrast, in Examples 9-18, a solvent system at a lower temperature was used for the oleoyl ethanolamide synthesis. A solvent was used to make the final product dispersed (melting point of 95° C.) at a temperature that will not significantly denature the enzyme, so that in practice the enzyme can be reused. Plastina et al., *Lett. Org. Chem.* 6:444-47 (2009), which is hereby incorporated by reference in its entirety also used hexane as the solvent to synthesize oleoyl ethanolamide, but the reaction at ambient temperature resulted in a longer reaction time and low oleic acid conversion. Further, preparative HPLC was used in Plastina et al. for the purification of oleoyl ethanolamide, which is unsuitable for a large-scale synthesis. In addition, pure oleic acid was used in Plastina et al. for the oleoyl ethanolamide synthesis, which is rather expensive. Compared to the method in Plastina et al., having 90% 18:1 oleic acid conversion and 88% oleoyl ethanolamide yield on a small scale, Examples 9-18 showed that purer ethanolamide can be obtained with almost 100% oleic acid conversion and more than 95% oleoyl ethanolamide yield. This method can be scaled to 50 mmol for each of reactants. Further, much less lipase, 30% compared to 65% in Plastina et al. was used. In addition, the results in Examples 9-18 have demonstrated that recrystallization is a much simpler and scalable method for oleoyl ethanolamide purification at a large scale compared to the preparative HPLC. This recrystallization step is unique and has not been reported by others. Therefore, the procedures and efficiency of the synthesis and product purification have been significantly improved over the existing work.

The amidation reaction could also be conducted in the presence of a condensation agent, such as 1-ethyl-3-(3-dimethylaminopropyl)carbodiimide hydrochloride (Williams et al., *Anal. Chem.* 79:5582-93 (2007), which is hereby incorporated by reference in its entirety). However, this agent is toxic, thus undesirable.

The synthesis method described in Examples 9-18 is effective and scalable. It is economical as oleic acid can be purified by crystallization from methanol instead of using a commercially pure oleic acid. It is effective and efficient as an enzyme was used as the catalyst and the reaction proceeded to an almost complete. The commercially available pure oleoyl ethanolamide is very expensive ($144 per 10 mg, from Sigma Aldrich Chemical Company), which may limit the study of biological and nutritional properties of oleoyl ethanolamide. The method described herein allows the production of this compound in a large quantity with a low cost.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for making a fatty acid N-acylalkanolamine having the formula:

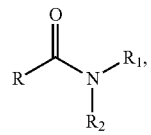

wherein

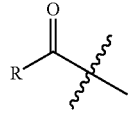

is derived from a natural or synthetic fatty acid;
$R_1$ is a substituted or unsubstituted $C_1$ to $C_{10}$ hydroxyalkyl;
$R_2$ is H, $R_1$ or a $C_1$ to $C_{10}$ hydrocarbon radical,
said method comprising:
providing a fatty acid;
purifying the fatty acid;
providing a primary or secondary alkanolamine having the formula: $NHR_1R_2$;
reacting the purified fatty acid with the alkanolamine under the condition effective to form the fatty acid N-acylalkanolamine; and
purifying the formed fatty acid N-acylalkanolamine.

2. The method of claim 1, wherein the alkanolamine is selected from the group consisting of ethanolamine, propanolamine, isopropanolamine, butanolamine, isobutanolamine, methylethanolamine, butylethanolamine, and mixtures thereof.

3. The method of claim 1, wherein the alkanolamine is ethanolamine.

4. The method of claim 3, wherein the fatty acid N-acylalkanolamine is a fatty acid N-acylethanolamine.

5. The method of claim 1, wherein the fatty acid contains from about 4 to about 26 carbon atoms.

6. The method of claim 5, wherein the fatty acid is an unsaturated fatty acid.

7. The method of claim 6, wherein the fatty acid is selected from the group consisting of oleic acid, myristoleic acid, palmitoleic acid, sapienic acid, elaidic acid, vaccenic acid, linoleic acid, linoelaidic acid, α-linolenic acid, arachidonic acid, eicosapentaenoic acid, erucic acid, docosahexaenoic acid, and mixtures thereof.

8. The method of claim 6, wherein the fatty acid is oleic acid.

9. The method of claim 1, wherein said reacting is carried out in the presence of at least one solvent.

10. The method of claim 9, wherein the solvent is hexane.

11. The method of claim 9, wherein the solvent is present in a concentration ranging from 30 to 85 wt % of all total reactants.

12. The method of claim 9, wherein the solvent is present in a concentration ranging from 30 to 60 wt % of all total reactants.

13. The method of claim 1, wherein said reacting is carried out with at least one catalyst.

14. The method of claim 13, wherein the catalyst is a lipase.

15. The method of claim 14, wherein the lipase is present in a concentration ranging from 10 to 50 wt % of all total reactants.

16. The method of claim 14, wherein the lipase is present in a concentration ranging from 20 to 30 wt % of all total reactants.

17. The method of claim 13, wherein the catalyst is used with a moisture content ranging from 0.05 to 3 wt % of all total reactants.

18. The method of claim 13, wherein the catalyst is used with a moisture content ranging from 0.1 to 2 wt % of all total reactants.

19. The method of claim 1, wherein said reacting is carried out at a temperature lower than 90° C.

20. The method of claim 1, wherein said reacting is carried out at a temperature ranging from 60 to 75° C.

21. The method of claim 1, wherein said reacting is carried out in less than 5 hours.

22. The method of claim 1, wherein said reacting is carried out from 2 hours to 3 hours.

23. The method of claim 1, wherein said purifying the fatty acid is carried out by low-temperature crystallization.

24. The method of claim 1, wherein said purifying the formed fatty acid N-acylalkanolamine is carried out by recrystallization.

\* \* \* \* \*